(12) United States Patent
Zhu et al.

(10) Patent No.: US 8,906,927 B2
(45) Date of Patent: Dec. 9, 2014

(54) PENTA-SUBSTITUTED TETRAHYDROPYRIMIDINES WITH AGGREGATION-INDUCED EMISSION CHARACTERISTICS AND PREPARATION METHOD AND USE THEREOF

(75) Inventors: Qiuhua Zhu, Guangzhou (CN); Shuwen Liu, Guangzhou (CN)

(73) Assignee: Southern Medical University (CN)

( * ) Notice: Subject to any disclaimer, the term of this patent is extended or adjusted under 35 U.S.C. 154(b) by 0 days.

(21) Appl. No.: 14/113,694

(22) PCT Filed: Dec. 24, 2011

(86) PCT No.: PCT/CN2011/184601
§ 371 (c)(1),
(2), (4) Date: Oct. 24, 2013

(87) PCT Pub. No.: WO2012/155516
PCT Pub. Date: Nov. 22, 2012

(65) Prior Publication Data
US 2014/0051855 A1 Feb. 20, 2014

(30) Foreign Application Priority Data

May 19, 2011 (CN) .......................... 2011 1 0129857

(51) Int. Cl.
| | | |
|---|---|---|
| C09K 11/06 | (2006.01) | |
| C07D 239/06 | (2006.01) | |
| C07D 401/04 | (2006.01) | |
| H01L 51/05 | (2006.01) | |
| H01L 51/50 | (2006.01) | |
| H01L 51/00 | (2006.01) | |

(52) U.S. Cl.
CPC ............... *C09K 11/06* (2013.01); *H01L 51/50* (2013.01); *C07D 239/06* (2013.01); *C07D 401/04* (2013.01); *H01L 51/5012* (2013.01); *H01L 51/005* (2013.01); *C09K 2211/1007* (2013.01); *C09K 2211/1011* (2013.01); *C09K 2211/1044* (2013.01)
USPC ....................................................... 514/256

(58) Field of Classification Search
CPC .... C09K 11/06; C09D 239/06; C09D 401/04; H01L 51/05; H01L 51/50
USPC ....................................................... 514/256
See application file for complete search history.

(56) References Cited

U.S. PATENT DOCUMENTS

2008/0220407 A1 9/2008 Tang et al.
2010/0009362 A1 1/2010 Tang et al.

FOREIGN PATENT DOCUMENTS

| CN | 101659865 A | 3/2010 | |
|---|---|---|---|
| CN | 102250015 | * 11/2011 | ........... C07D 239/06 |
| CN | 102250015 A | 11/2011 | |
| JP | 2010112777 A | 5/2010 | |
| WO | 2004039786 A1 | 5/2004 | |

OTHER PUBLICATIONS

An, et al., "JACS Articles", J. Am. Chem. Soc. 2002, 124(48), 14410-14415.
Chan, et al., J. Am. Chem. Soc., 2002, 124(22), 6469-6479.
Chen, et a;., "Glucosamine hydrochloride funcionalized tetraphenylethylene: A novel fluorescent probe for alkaline phosphatase based on the aggregation-induced emission", ChemComm, 2010, 46, pp. 4067-4069.
Chen, et al., Chem. Mater., 2003, 15, 1535-1546.
Friend, et al., "Electroluminescence in conjugated polymers", Nature, Jan. 14, 1999, vol. 397, pp. 121-128.
Han, et al., J. Phys. Chem. C., 2010, 114(43), 18702-18711.
Hong, et al., Chem. Commun., 2009, (29), 4332-4353.
Zhao, et al., Curr. Org. Chem., 2010, 14(18), 2109-2132.
International Search Report for Application No. PCT/CN2011/084601 dated Feb. 23, 2012.
Itami, et al., "JOC Article", J. Org. Chem., 2005, 70(7), 2778-2792.
Jenekhe, et al., Science, New Series, vol. 265, No. 5173, Aug. 5, 1994, pp. 765-768.
Kamino, et al., Chem. Commun., 2010, 46, 9013-9015.
Lee, et al., J. Am. Chem. Soc., 2005, 127(25), 9071-9078.
Li, et al., J. Mater. Chem. 2011, 21(11), 3760-3767.

(Continued)

*Primary Examiner* — Erich A Leeser

(74) *Attorney, Agent, or Firm* — Lerner, David, Littenberg, Krumholz & Mentlik, LLP

(57) ABSTRACT

The present invention provides a series of penta-substituted tetrahydropyrimidines with aggregation-induced emission (AIE) characteristics and preparation method and use thereof. The AIE penta-substituted tetrahydropyrimidines have structures shown as formula (I). $R^1$ is selected from a group consisting of linear or branched alkyls and substituted alkyls. $R^2$ and $R^4$ is respectively selected from a group consisting of linear or branched alkyls, substituted alkyls, cycloalkyls, substituted cycloalkyls, aryls, substituted aryls, polycyclic aryls, substituted polycyclic aryls, heterocyclyls, substituted heterocyclyls, aromatic heterocyclyls and substituted aromatic heterocyclyls. $R^3$ is selected from a group consisting of aryls, substituted aryls, polycyclic aryls, substituted polycyclic aryls, aromatic heterocyclyls and substituted aromatic heterocyclyls. The penta-substituted tetrahydropyrimidines can be prepared by multi-component reactions (MCR). There are 1~3 aryls in the structure of the penta-substituted tetrahydropyrimidines. The penta-substituted tetrahydropyrimidines possess strong AIE properties and can be used for preparing organic electro-luminescence or photo-luminescence devices, or chemical and biological fluorescent sensors or probes.

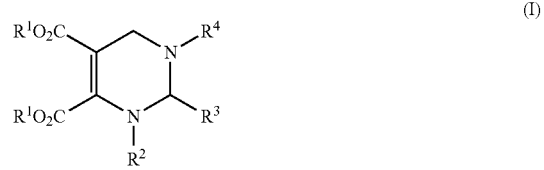

(I)

10 Claims, 5 Drawing Sheets

(56) References Cited

OTHER PUBLICATIONS

Liu, et al., "Fluorescent Chemosensor for Detecion and Quantitation of Carbon Dioxide Gas", Jacs Communication, Sep. 20, 2010, vol. 132, No. 40, pp. 13951-13953.
Liu, et al., "Simple Biosensor with High Selectivity and Sensitivity: Thiol-Specific Biomolecular Probing and Intracellular Imaging by AIE Fluorogen on a TLC Plate through a Thiol-Ene Click Mechanism" Chem. Eur. J., 2010, 16, 8433-8438.
Liu, et al., J. Inorg. Organomet, P.2009, 19(3), 249-285.
Liu, et al., J. Phys. Chem. C., 2008, 112(10), 3975-3981.
Luo, et al., Chem. Commun. , 2001, (18), 1740-1741.
Luo, et al., Chem. Commun. 2001, 18, 1740-1741.
Peng, et al., Org. Lett., 2009, 11(17), 4014-4017.
Qin,et al., "Polytriazoles wih Aggregation-Induced Emission Characteristics: Synthesis by Click Polymerization and Application as Explosive Chemosensors", Macromolecules, Jan. 19, 2009, vol. 42, No. 5, pp. 1421-1424.
Sartin, et al., J. Am. Chem. Soc., 2006, 128(31), 10163-10170.
Tang, et al., "A fluorescent thermometer operating in aggregaion-induced emission mechanism: proding thermal transitions of PNIPAM in water", ChemComm, 2009, pp. 4974-4976.
Tang, et al., "JOC Notes", J. Org. Chem., 2009, 74, 2163-2166.
Tang, et al., J. Mater. Chem., 2001, 11, 2974-2978.
Tong, et al., Chem. Commun., 2006, (35), 3705-3707.
Tong, et al., J. Phys. Chem. C, 2007, 111, 2287-2294.
Tracy, et al., Inorg. Chem., 2005, 44(6), 2003-2011.
Wang, et al., "Sugar-bearing tetraphenylethylene: novel fluorescent probe for studies of carbohydrate-protein interaction based on aggregation-induced emission", Organic & Biomolecular Chemistry, 2011, 9, pp. 2219-2226.
Wang, et al., Chem-Eur. J. 2011, 17 (9), 2647-2655.
Wang, et al., J. Mater. Chem., 2010 20(10), 1858-1867.
Xue, et al., Org. Lett., 2010, 12(10), 2274-2277.
Yu, et al., J. Am. Chem. Soc., 2005, 127, 6335-6346.
Zeng, et al., Chem. Commun., 2007, 70-72.
Zhang; Shuang et al., Mechanism Study of Aggregation-Induced Emission, Progress in Chemistry, Apr. 2011, vol. 23, No. 4, pp. 623-636.
Zhao, et al., Angew. Chem. Int. Ed. 2009, 48, 7608-7611.

* cited by examiner

PENTA-SUBSTITUTED TETRAHYDROPYRIMIDINES WITH AGGREGATION-INDUCED EMISSION CHARACTERISTICS AND PREPARATION METHOD AND USE THEREOF

CROSS-REFERENCE TO RELATED APPLICATIONS

The present application is a national phase entry under 35 U.S.C. §371 of International Application No. PCT/CN2011/084601 filed on Dec. 24, 2011, published in Chinese, which claims the benefit of Chinese Patent Application No. 201110129857.X, filed on May 19, 2011. The disclosures of all of said applications are incorporated herein by reference.

FIELD OF THE INVENTION

The present invention relates to organic luminescent materials, and in particular, to a series of penta-substituted tetrahydropyrimidines with aggregation-induced emission (AIE) characteristics and preparation method and use thereof.

BACKGROUND OF THE INVENTION

Most of the organic fluorescent compounds show good luminescnt properties in dilute solutions. However, when they are in aggregation state, especially in crystalline state, the fluorescence declines or even quenches. This is because molecule interaction increases with the increase of concentration of fluorescent substance, resulting in decrease of fluorescence intensity because of easy formation of excimers between same molecules or exciplexes between different molecules (Nature, 1999, 397, 121-128; Science, 1994, 265, 765-768).

Especially for organic fluorescent molecules with rigid big planar structures, they show strong fluorescence in solutions but very weak fluorescence in aggregates. This phenomenon is known as the aggregation-caused quenching (ACQ) of fluorescence. ACQ restricts the use of fluorescent substances in preparing organic light-emitting diodes (OLED), chemical and biological sensors and in other fields. For example, when manufacturing OLED, which has advantages of low driving voltage, light weight, all-solid self-luminous property, extremely thin thickness, strong brightness, high efficiency, quick responding speed, wide viewing angle, potentiality to make flexible bendable display panel and suitability for large area display, it requires the organic luminescent material to be made into thin solid films or other aggregation forms, which inevitably lead to ACQ and affect the luminous efficiency of the organic fluorescent substance and the service life of the OLED.

As for the use in fluorescent sensors or probes, the concentration of the fluorescent substance used for fluorescent sensors or probes have to be maintained in a very low level because of ACQ, which reduces the accuracy of the method when it is used for quantitative analysis. In addition, the aggregation of the fluorescent substances in active sites of biological macromolecules also significantly affects the accuracy of the detecting method.

Therefore, ACQ has always been a problem that is difficult to overcome but must be resolved in the use of organic fluorescent substance. For a long time, various chemical and physical methods and processing technologies have been used to try to reduce the ACQ of fluorescent substances. However, very limited results were achieved.

In the process of developing various new luminescent materials with more excellent performance, TANG Benzhong and his research group in 2001 found compound silole I (see compound I in FIG. 1) that is not luminous in solutions but shows very strong luminescent property in solid state (Chem. Commun. 2001, 18, 1740-1741; J. Mater. Chem., 2001, 11, 2974-2978). They named this phenomenon as aggregation-induced emission (ATE).

The discovery of AIE phenomenon provides a fundamental solution for the short life of OLED and low detection accuracy of fluorescent sensors or probes caused by ACQ. Therefore, organic fluorescent substances with AIE properties has quickly became the object of studies in fields such as synthetic organic chemistry, luminescent material chemistry, biochemistry, analytical chemistry, etc. In the recent ten years, organic fluorescent substances with AIE properties have showed unique advantages in fields such as OLEDs (Patent CN101659865A, 2010; J. Phys. Chem. C. 2008, 112 (10), 3975-3981; J. Am. Chem. Soc. 2002, 124 (22), 6469-6479; J. Am. Chem. Soc. 2005, 127(25), 9071-9078; J. Am. Chem. Soc. 2006, 128(31), 10163-10170), fluorescence sensors (Patent US20080220407A1, 2008; Patent US20100009362A1, 2010; Patent JP2010112777A, 2010; J. Am. Chem. Soc. 2010, 132(40), 13951-13953; Macromolecules 2009, 42(5), 1421-1424; Chem. Commun. 2009, (33), 4974-4976), fluorescent probes (Org. Biom. Chem. 2011, 9(7), 2219-2226; Chem. Commun. 2010, 46(23), 4067-4069; Chem-Eur. J. 2010, 16(28), 8433-8438; Chem. Commun. 2009, (33), 4974-4976; Chem. Commun. 2006, (35), 3705-3707) and biology activity examinations (Org. Lett. 2009, 11(17), 4014-4017; Org. Lett. 2010, 12(10), 2274-2277) (Curr. Org. Chem. 2010, 14(18), 2109-2132; J. Mater. Chem. 2010, 20(10), 1858-1867; Chem. Commun. 2009, (29), 4332-4353; J. Inorg. Organomet. P. 2009, 19(3), 249-285).

Although organic fluorescent substances with AIE properties have broad application prospects in various fields, there are very few types of such compounds. TANG Benzhong and his research group deeply studied the factors that affect the AIE property and the reason why it happens, and proposed the mechanism for generating A1E phenomenon. They think that AIE molecules are not luminous in solutions because they can decay non-radiatively by rotation or vibration of benzene, and becomes luminous in solids because they decay in a radiative form owing to the restriction of the rotation or vibration in aggregates (Angew. Chem. Int. Ed. 2009, 48, 7608-7611; J. Am. Chem. Soc, 2005, 127, 6335-6346; Chem. Mater., 2003, 15, 1535-1546; J. Phys. Chem. C, 2007, 111, 2287-2294).

The known AIE molecular structures have the following two characteristics: (1) the molecule contains at least two or more rotatable and conjugated rigid aromatic rings; (2) the steric effect generated by these aromatic rings makes the whole molecule become a twisted non-planar spatial configuration, instead of the rigid planar spatial molecular configuration of normal organic fluorescent compounds. The results achieved by TANG Benzhong and his research group act as a guide to the design and synthesis of AIE molecules. Many compounds with aggregation induced emission enhancement (AIEE) have been developed in recent years. These compounds have luminescence in solution and their luminescence increases (generally less than 100 times) in aggregation state (J. Mater. Chem. 2011, 21(11), 3760-3767; Chem-Eur. J. 2011, 17(9), 2647-2655; Chem. Commun. 2010, 46(47), 9013-9015; J. Phys. Chem. C, 2010, 114 (43), 18702-18711). But there are very few compounds with AIE property, i.e., compounds that have almost no luminescence in solution but become luminous in aggregation state. There are only a few AIE compounds whose luminous intensity in aggregation state is stronger than their luminous intensity in solution by two orders of magnitude, such as compound I and compound III in FIG. 1.

Based on whether the aromatic rings are connected by single bonds to the double bonds inside the rings or outside the rings, the AIE compounds can be divided into cyclic compounds and chain compounds. Since the cyclic AIE compounds are more difficult to be synthesized than chain AIE compounds, most of the reported AIE compounds are chain compounds. Cyclic AIE compounds are mainly multi-phenyl silicone heterocyclic compounds Silole (such as compound I in FIG. 1, whose fluorescence quantum yield in aggregation state is 330 times more than the fluorescence quantum yield in solution) discovered by TANG Benzhong and his research group (Chem. Commun. 2001, (18), 1740-1741). The replacement of Si atom in Silole by Ge and Sn atoms also provides certain AIE property. But the AIE effect is very weak and the fluorescence quantum yield in aggregation state is only increased by several times (Inorg. Chem. 2005, 44(6), 2003-2011).

Most of the chain AIE compounds can be represented by multi-phenyl vinyl compounds, such as compound II (J. Org. Chem. 2005, 70(7), 2778-2792) and III (J. Am. Chem. Soc. 2002 124(48), 14410-14415) in FIG. 1. There are also some specially structured AIE compounds, such as compounds IV and V, in which two or more benzene rings are connected directly by single bonds and form a conjugated system (the fluorescence wavelength of this kind of compounds is in the non-visible region of the ultraviolet region and the fluorescence quantum yield in aggregation state and in solution are not measured, Chem. Commun., 2007, 70-72), and compound VI with C=N double bonds in the conjugated system (J. Org. Chem. 2009, 74, 2163-2166). Because of the wide use of AIE compounds, it is necessary to develop more AIE fluorescent compound with good luminous efficiency.

SUMMARY OF THE INVENTION

An object of the present invention is to provide a series of aggregation-induced luminescent penta-substituted tetrahydropyrimidines with AIE characteristics and novel molecular structures. The fluorescence quantum yields of the penta-substituted tetrahydropyrimidines in aggregates are stronger than those in solutions by up to 5535 times. Another object of the present invention is to provide a preparation method for said AIE penta-substituted tetrahydropyrimidines. This method is carried out by a multi-component reaction (MCR) with easily obtainable materials, wide application scope of substrates, and simple and convenient steps. Huge amount of AIE penta-substituted tetrahydropyrimidines can be prepared by the MCR efficiently and easily.

Another object of the present invention is to provide use of said AIE penta-substituted tetrahydropyrimidines.

To achieve the mentioned-above objects, penta-substituted tetrahydropyrimidine with aggregation-induced emission characteristics having structures shown as formula (I) are provided:

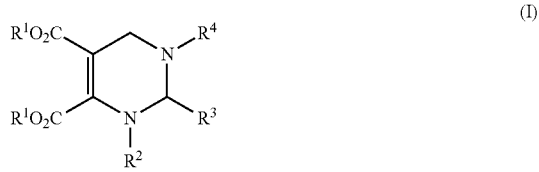

Wherein:
$R^1$ is selected from a group consisting of $C_{1-8}$ linear or branched alkyls and $C_{1-8}$ substituted alkyls;

$R^2$ and $R^4$ are independently selected from a group consisting of $C_{1-8}$ linear or branched alkyls, $C_{1-8}$ substituted alkyls, $C_{5-8}$ cycloalkyls, $C_{5-8}$ substituted cycloalkyls, $C_{5-6}$ aryls, $C_{5-6}$ substituted aryls, $C_{9-18}$ polycyclic aryls, $C_{9-18}$ substituted polycyclic aryls, $C_{5-6}$ heterocyclyls, $C_{5-6}$ substituted heterocyclyls, $C_{5-6}$ aromatic heterocyclyls and substituted aromatic heterocyclyls;

$R^3$ is selected from a group consisting of $C_{5-6}$ aryls, $C_{5-6}$ substituted aryls, $C_{9-18}$ polycyclic aryls, $C_{9-18}$ substituted polycyclic aryls, $C_{5-6}$ aromatic heterocyclyls and $C_{5-6}$ substituted aromatic heterocyclyls.

In a preferable embodiment, $R^1$ is selected from a group consisting of $C_{1-2}$ alkyls.

In a preferable embodiment, $R^2$ is selected from a group consisting of $C_{1-5}$ linear or branched alkyls, $C_{1-5}$ substituted alkyls, $C_{5-8}$ cycloalkyls, $C_{5-6}$ aryls and $C_{5-6}$ substituted aryls.

In a preferable embodiment, $R^3$ is selected from a group consisting of $C_{5-6}$ aryls and $C_{5-6}$ substituted aryls.

In a preferable embodiment, $R^4$ is selected from a group consisting of $C_{1-5}$ linear or branched alkyls, $C_{1-5}$ substituted alkyls, $C_{5-8}$ cycloalkyls, $C_{5-6}$ aryls and substituted aryls. In a preferable embodiment, the substituents mentioned above are selected from a group consisting of halogens, $C_{1-2}$ perhalogenated alkyls, $C_{1-4}$ halogenated alkyls, hydroxyl, $C_{1-6}$ linear or branched alkoxys, nitryl, cyano, amino, $C_{1-6}$ monoalkyl aminos, $C_{1-6}$ dialkyl aminos, $C_{5-8}$ monocyclic alkyl aminos, $C_{5-6}$ monoheterocyclyl aminos, $C_{5-6}$ monoaryl aminos, $C_{1-6}$ alkyl aminos, $C_{5-6}$ aryl amidos, amino carbonyls, $C_{1-6}$ monoalkyl amino carbonyls, $C_{1-6}$ dialkyl amino carbonyls, $C_{1-6}$ alkyl acyls, $C_{5-8}$ aryl acyls, amino sulfones, $C_{1-6}$ monoalkyl amino sulfones, $C_{1-6}$ dialkyl amino sulfones, $C_{5-8}$ aryl amino sulfones, $C_{1-6}$ alkyl sulfonyl aminos, carboxyl, $C_{1-6}$ monoalkyl sulfones, linear or branched alkyls, $C_{5-8}$ cycloalkyls, $C_{5-8}$ substituted cycloalkyls, $C_{2-4}$ alkenyls, $C_{2-4}$ alkynyls, aryl $C_{1-3}$ alkyls, $C_{5-6}$ aryls, $C_{5-6}$ substituted aryls, $C_{9-18}$ polycyclic aryls, $C_{5-6}$ heterocyclyls, $C_{5-6}$ aromatic heterocyclyls and $C_{9-18}$ polycyclic aromatic heterocyclyls.

In a preferable embodiment, in formula (I), $R^1$ is methyl or ethyl;
$R^2$ is selected from a group consisting of phenyl, benzyl, methyl phenyl, chlorophenyl, bromophenyl, trifluoromethyl phenyl, n-butyl;
$R^3$ is selected from a group consisting of phenyl, bromophenyl, methoxy hydroxy substituting phenyl, bromophenyl, trifluoromethyl phenyl, naphthyl, pyridyl; and
$R^4$ is selected from a group consisting of phenyl, benzyl, methyl phenyl, chlorophenyl, bromophenyl, trifluoromethyl phenyl, hydroxyethyl, n-butyl.

The present invention also provides a preparation method for said penta-substituted tetrahydropyrimidines with aggregation-induced emission characteristics, comprising steps of (by mmol parts):

(1) adding 1 part of formula (II) compound and 1 part of formula (III) compound into 1~10 mL of organic solvent, followed by stirring at 0~60° C. for 10~60 minutes;

(2) adding 1~5 parts of formula (IV) compound, 1~5 parts of formaldehyde and then 0~4 parts of acid into 1~10 mL of organic solvent, followed by stirring at 20~100° C. for 10 minutes ~5 hours;

(3) mixing solutions obtained by steps (1) and (2), then adding 1~5 parts of formula (V) compound and 0.1~0.5 parts of catalyst, followed by stirring at −15~100° C. for 1~7 days, separating and purifying to obtain a product; wherein $$R^1OOC \longequal COOR^1 \qquad (II),$$

$$R^2NH_2 \qquad (III),$$

R⁴NH₂    (IV),

R³CHO    (V);

The acid is hydrochloric acid, sulfuric acid, phosphoric acid, benzenesulfonic acid, trifluoroacetic acid, acetic acid or a mixture thereof;

The catalyst is copper sulfate, copper acetate, zinc chloride, palladium acetate, thiourea, praline, urea or a mixture thereof;

The organic solvent is ethanol, benzene, toluene, hexane, halogenated hydrocarbons, ethers, N,N-dimethylformamide, dimethyl sulfoxide, acetonitrile or a mixture thereof.

The present invention also provides use of said penta-substituted tetrahydropyrimidines with aggregation-induced emission characteristics in preparing organic electro-luminescence or photo-luminescence devices. The penta-substituted tetrahydropyrimidines can be used as materials of luminescent layers of organic electro-luminescence or photo-luminescence devices.

The present invention also provides use of said penta-substituted tetrahydropyrimidines with aggregation-induced emission characteristics in preparing chemical and biological fluorescent sensors or probes.

The penta-substituted tetrahydropyrimidines with AIE property in the present invention are a series of new compounds, with structures totally different from the existing compounds with AIE property. While there are 1~3 aryls in the molecules of this series of compounds, the aryls do not form a conjugated system as the aryls in the existing AIE compounds. Even if there is only one aryl in the molecule, e.g., 1,3-dibutyl-1,2,3,6-tetrahydro-2-phenylpyrimidine-4,5-dicarboxylate, the compound still have very strong AIE property. This serious of compounds are AIE compounds with the lowest conjugation degree to date.

The penta-substituted tetrahydropyrimidines in the present invention show totally no fluorescence in solutions such as tetrahydrofuran, dichloromethane, ethyl acetate or ethanol, but show very strong fluorescence in mixed solution (ethanol-water=1:9) and in crystalline state. The fluorescence intensities of the penta-substituted tetrahydropyrimidines in aggregates are stronger than those in solutions by up to 5535 time, which is stronger than the AIE property of the compound III in FIG. 1. The fluorescence quantum yields of the penta-substituted tetrahydropyrimidines in aggregates are up to 0.8, which is higher than that of the compound III in FIG. 1 (which is 0.69).

A five-component reaction (5CR) is used in the present invention to prepare the penta-substituted tetrahydropyrimidines. The 5CR possesses advantages of atom economy, easily obtainable materials, easy operation, high productivity and various structures of products. Theoretically, $10^8$ products of different structures can be produced by a four-component reaction with 100 kinds of each component. The synthesis method in the present invention is about an 5CR with easily obtainable materials, wide application scope of substrates and simple and convenient steps, thus can be used to prepare huge amount of penta-substituted tetrahydropyrimidines with strong AIE property.

Therefore, compared to the existing methods for preparing compounds with AIE property, the method in the present invention show incomparable advantages in the ability and speed in developing new AIE compounds. Since different molecule structure has different fluorescence spectrum, the method in the present invention can be used to synthesize AIE fluorescent compound with various emission wavelength.

The present invention is advantageous over conventional techniques as follows:

(1) There are 1~3 aryls in the structure of the penta-substituted tetrahydropyrimidine, providing it with very strong AIE property. The fluorescence intensities of the penta-substituted tetrahydropyrimidine in aggregation state is stronger than those in solutions by up to 5535 time;

(2) 5CR is used in the present invention to prepare penta-substituted tetrahydropyrimidines with AIE property. Compared to the existing methods for preparing compounds with AIE property, the method in the present invention show incomparable advantages in the ability and speed in developing new AIE compounds.

DETAILED DESCRIPTION OF THE INVENTION

Figure 1:
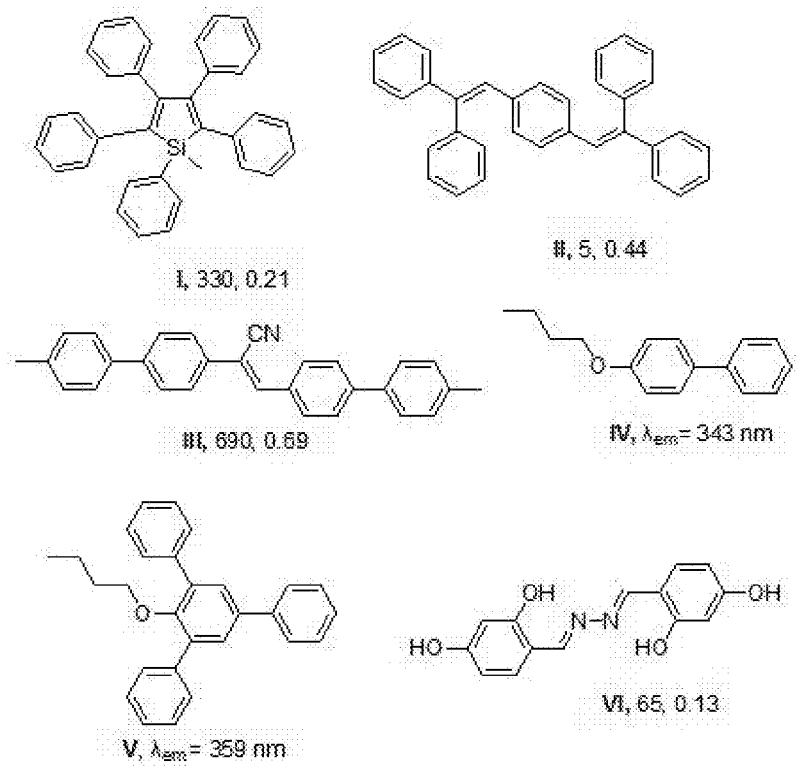
FIG. 1 shows examples of existing compounds with AIE property, wherein the numbers following the compound numbers are the ratio between the fluorescence quantum yield in aggregaes and that in solution, and the fluorescence quantum yield in aggregates, respectively.

The present invention will be further illustrated by example embodiments, whereas the examples are not intended to be limiting the present invention in any form.

Example 1

(1) 1 mmol (170 mg) of diethyl acetylenedicarboxylate and 1 mmol (93 mg) of aniline were successively added into 2 mL of ethanol, which was then stirred at room temperature by 20 min.
(2) 2 mmol (186 mg) of aniline, 2 mmol (160 mg) of aqueous formaldehyde (30% wt %) and 2 mmol (120 mg) of acetic acid were added into 2 mL of ethanol, which was then stirred at 40° C. by 20 min.

Figure 2:
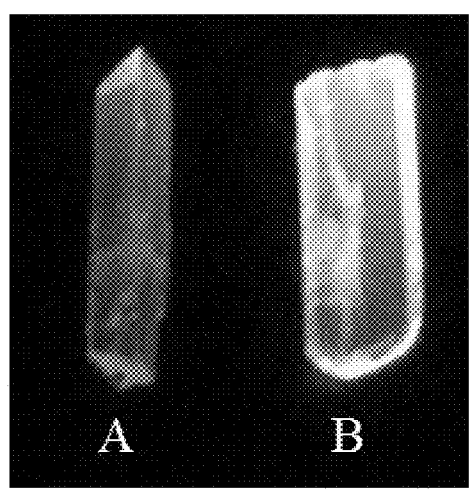
FIG. 2 shows the luminescence of the white and light green crystals of the compound in Example 1 at λ=365 nm, wherein the white crystal A shows blue fluorescence while the light green crystal B shows green fluorescence.
Figure 3:
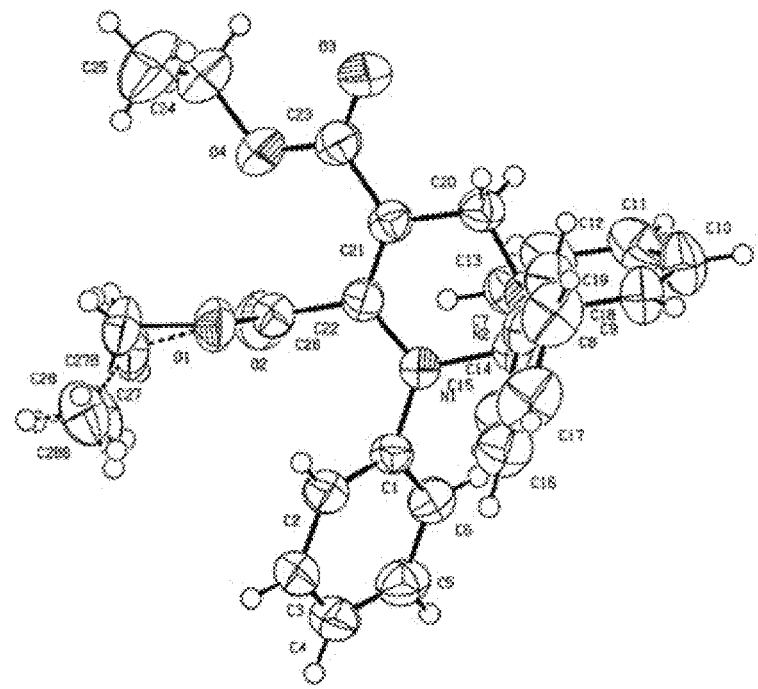
FIG. 3 shows the X-ray diffraction analysis result of a single crystal of the compound emitting blue fluorescence at λ=−365 nm in Example 1. The registration number of the compound in Cambridge Crystallographic Data Centre (CCDC) is CCDC 818027.
Figure 4:
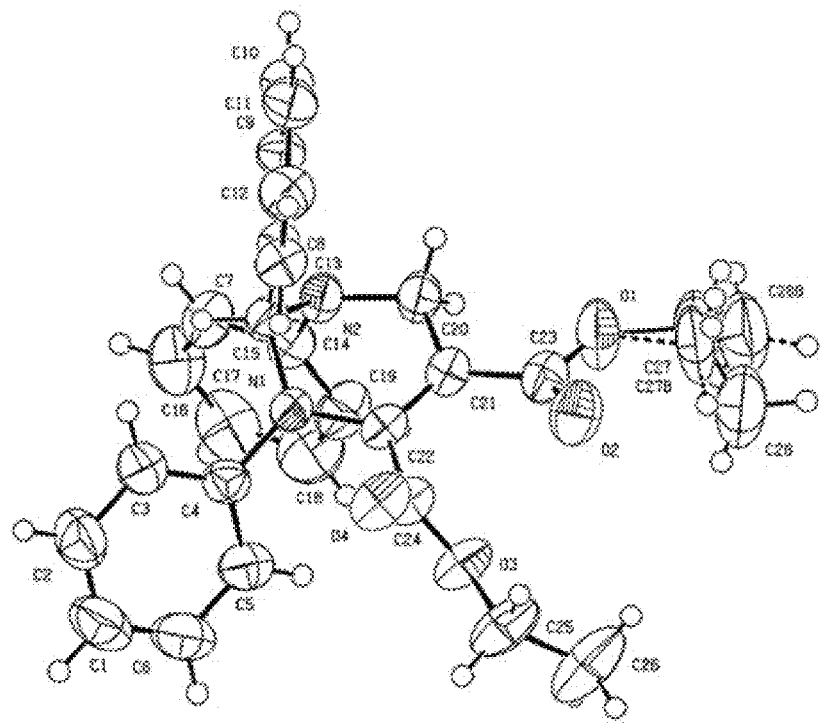
FIG. 4 shows the X-ray diffraction analysis result of a single crystal of the compound emitting green fluorescence at λ=365 nm in Example 1. The registration number of the compound in CCDC is CCDC 818026.

The solutions obtained by (1) and (2) were mixed, and then added with 2 mmol (212 mg) of benzaldehyde and 0.1 mmol (6 mg) of urea at 40° C. After 48 h of reaction, 20 mL of saturated aqueous sodium chloride was added. Then extraction with 20 mL of dichloromethane was repeated 3 times. The dichloromethane solutions were mixed and then extracted with 20 mL of saturated aqueous sodium chloride by 3 times. The resulting dichloromethane solution was dried with magnesium sulfate, and then subjected to distillation under reduced pressure to remove the solvent. The product was purified by preparative layer chromatography, using n-hexane+ethyl acetate (10:1) as the developing agent and ethyl acetate as the eluting agent. Vacuum rotary evaporation was performed to remove the solvent and 246 mg of diethyl 1,2,3,6-tetrahydro-1,2,3-triphenylpyrimidine-4,5-dicarboxylate (Compound 1) was obtained. The compound was recrystallized and hence both the white crystal that shows blue fluorescence at 365 nm wavelength and the light green crystal that shows green fluorescence at 365 nm wavelength were obtained (see FIG. 2). The X-ray diffraction analysis results of the white and green single crystals were shown in FIGS. 3 and 4.

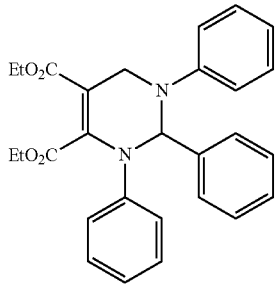 [SMILES: CCOC(=O)C1=C(C(=O)OCC)N(c2ccccc2)C(c2ccccc2)N(c2ccccc2)C1]

diethyl 1,2,3,6-tetrahydro-1,2,3-triphenylpyrimidine-4,5-dicarboxylate, Compound 1; yield=54%, white crystal that shows blue fluorescence, melting point=129.6-130.5° C.; light green crystal that shows green fluorescence, mp=119.5~120.5° C.; IR (KBr): vmax=2980, 1739, 1697, 1592, 1495, 1234, 1108, 761, 696 cm$^{-1}$; $^1$H NMR (400 MHz, CDCl$_3$): δ=7.67-6.90 (m, 15H), 6.12 (s, 1H), 4.30 (d, J=17.6 Hz, 1H), 4.12-4.07 (m, 4H), 3.61~3.56 (d, J=17.6 Hz, 1H), 1.22 (t, J=7.2 Hz, 3H), 1.03 (t, J=7.2 Hz, 3H) ppm; $^{13}$C NMR (101 MHz, CDCl$_3$): δ=165.45, 164.24, 149.57, 144.94, 144.44, 138.46, 129.35, 129.09, 129.07, 128.34, 126.99, 126.08, 124.46, 121.45, 118.98, 101.48, 79.87, 61.65, 60.16, 42.62, 14.22, 13.57 ppm; MS (ESI): m/z 457(M+H$^+$, 28), 276 (100); Anal. Calcd for C$_{28}$H$_{28}$N$_2$O$_4$: C, 73.66; H, 6.18; N, 6.14. Found: C, 73.91; H, 6.10; N, 6.21.

Example 2

(1) 1 mmol (170 mg) of diethyl acetylenedicarboxylate and 1 mmol (107 mg) of benzylamine were successively added into 1 mL of N,N-dimethylformamide, which was then stirred at room temperature by 10 min.
(2) 1 mmol (107 mg) of benzylamine and 1 mmol (80 mg) of formaldehyde (30%) were added into 2 mL of N,N-dimethylformamide, which was then stirred at room temperature by 10 min.
(3) The solutions obtained by (1) and (2) were mixed, and then added with 1 mmol (106 mg) of benzaldehyde and 0.5 mmol (55 mg) of proline at 80° C. After 24 h of reaction, 20 mL of saturated aqueous sodium chloride was added. Then extraction with 20 mL of dichloromethane was repeated 3 times. The dichloromethane solutions were mixed and then extracted with 20 mL of saturated aqueous sodium chloride by 3 times. The resulting dichloromethane solution was dried with magnesium sulfate, and then subjected to distillation under reduced pressure to remove the solvent. The product was purified by preparative layer chromatography, using n-hexane+ethyl acetate (10:1) as the developing agent and ethyl acetate as the eluting agent. Vacuum rotary evaporation was performed to remove the solvent and 140 mg of Compound 2 was obtained.

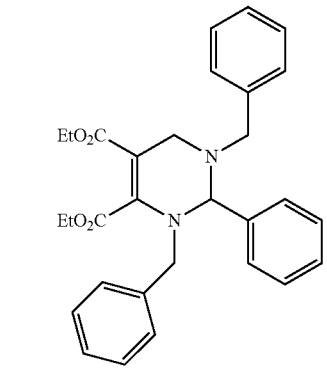 [SMILES: CCOC(=O)C1=C(C(=O)OCC)N(Cc2ccccc2)C(c2ccccc2)N(Cc2ccccc2)C1]

diethyl 1,3-dibenzyl-1,2,3,6-tetrahydro-2-phenylpyrimidine-4,5-dicarboxylate, Compound 2; yield=29%, white solid, melting point=107.2-108.0° C.; IR (KBr): v$_{max}$=2983, 2358, 1735, 1688, 1575, 1447, 1285, 1147, 1109, 746, 688 cm$^{-1}$; $^1$H NMR (400 MHz, CDCl$_3$): δ=7.43-7.06 (m, 15H), 4.79 (s, 1H), 4.57 (d, J=15.6 Hz, 1H), 4.54-4.50 (m, 2H), 4.13-4.09 (m, 2H), 4.01 (d, J=15.6 Hz, 1H), 3.69 (d, J=13.6 Hz, 1H), 3.44 (d, J=13.6 Hz, 1H), 3.39 (d, J=16.8 Hz, 1H), 3.26 (d, J=16.8 Hz, 1H), 1.47 (t, J=7.2 Hz, 3H), 1.22 (t, J=7.2 Hz, 3H) ppm; $^{13}$C NMR (101 MHz, CDCl$_3$): δ=166.50, 165.41, 147.75, 136.49, 128.88, 128.78, 128.72, 128.25, 128.16, 126.96, 91.06, 74.12, 62.32, 59.59, 57.68, 53.38, 42.56, 14.39, 14.06 ppm; MS (ESI):m/z 485 (M+67), 290 (100); Anal. Calcd for C$_{30}$H$_{32}$N$_2$O$_4$: C, 74.36; H, 6.66; N, 5.78. Found: C, 74.15; H, 6.71; N, 5.83.

Example 3

(1) 1 mmol (170 mg) of diethyl acetylenedicarboxylate and 1 mmol (107 mg) of p-toluidine were successively added into 1 mL of n-hexane, which was then stirred at room temperature by 1 h.
(2) 5 mmol (107 mg) of p-toluidine and 3 mmol (240 mg) of formaldehyde (30%) were added into 10 mL of dichloromethane, which was then stirred at room temperature by 10 min.
(3) The solutions obtained by (1) and (2) were mixed, and then added with 5 mmol (530 mg) of benzaldehyde and 0.5 mmol of copper acetate at room temperature. After 36 h of reaction, 20 mL of saturated aqueous sodium chloride was added. Then extraction with 20 mL of dichloromethane was repeated 3 times. The dichloromethane solutions were mixed and then extracted with 20 mL of saturated aqueous sodium chloride by 3 times. The resulting dichloromethane solution was dried with magnesium sulfate, and then subjected to distillation under reduced pressure to remove the solvent. The product was purified by preparative layer chromatography, using n-hexane+ethyl acetate (10:1) as the developing agent and ethyl acetate as the eluting agent. Vacuum rotary evaporation was performed to remove the solvent and 246 mg of Compound 3 was obtained.

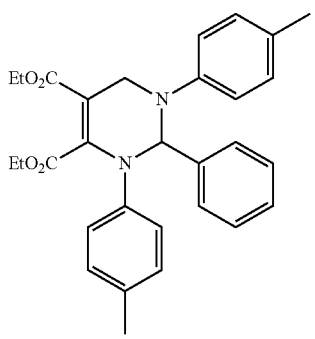 [SMILES: CCOC(=O)C1=C(C(=O)OCC)N(c2ccc(C)cc2)C(c2ccccc2)N(c2ccc(C)cc2)C1]

diethyl 1,2,3,6-tetrahydro-2-phenyl-1,3-dip-tolylpyrimidine-4,5-dicarboxylate, Compound 3; yield=51%, yellow solid, melting point=146.5-148.2° C.; IR (KBr): $v_{max}$=3059, 3029, 2924, 1740, 1698, 1595, 1511, 1423, 1390, 1289, 1234, 1107, 1007, 817, 760, 698 cm$^{-1}$; $^1$H NMR (400 MHz, CDCl$_3$): δ=7.66-6.84 (m, 13H), 5.99 (s, 1H), 4.22 (d, J=17.6 Hz, 1H), 4.19-4.07 (m, 4H), 3.55 (d, J=17.6 Hz, 1H), 2.27 (s, 3H), 2.26 (s, 3H), 1.21 (t, J=7.2 Hz, 3H), 1.06 (t, J=7.2 Hz, 3H) ppm; $^{13}$C NMR (101 MHz, CDCl$_3$) δ=165.58, 164.37, 147.38, 145.45, 141.78, 138.69, 135.99, 130.90, 129.84, 129.62, 128.98, 128.23, 127.07, 124.67, 119.30, 100.14, 80.19, 77.38, 77.06, 76.75, 61.58, 60.03, 42.69, 20.95, 20.61, 14.25, 13.63 ppm; MS (ESI): m/z 485 (M+31), 290 (100); Anal. Calcd for C$_{30}$H$_{32}$N$_2$O$_4$: C, 74.36; H, 6.66; N, 5.78. Found: C, 74.05; H, 6.61; N, 5.69.

Example 4

(1) 1 mmol (170 mg) of diethyl acetylenedicarboxylate and 1 mmol (127 mg) of p-chloroaniline were successively added into 1 mL of methanol, which was then stirred at 60° C. by 10 min.
(2) 1.5 mmol (190 mg) of p-chloroaniline and 1 mmol (80 mg) of formaldehyde (30%) were added into 10 mL of dichloromethane, which was then stirred at room temperature by 10 min.
(3) The solutions obtained by (1) and (2) were mixed, and then added with 1.5 mmol (159 mg) of benzaldehyde and 0.5 mmol (55 mg) of thiourea at room temperature. After 36 h of reaction, 20 mL of saturated aqueous sodium chloride was added. Then extraction with 20 mL of dichloromethane was repeated 3 times. The dichloromethane solutions were mixed and then extracted with 20 mL of saturated aqueous sodium chloride by 3 times. The resulting dichloromethane solution was dried with magnesium sulfate, and then subjected to distillation under reduced pressure to remove the solvent. The product was purified by preparative layer chromatography, using n-hexane+ethyl acetate (10:1) as the developing agent and ethyl acetate as the eluting agent. Vacuum rotary evaporation was performed to remove the solvent and 262 mg of Compound 4 was obtained.

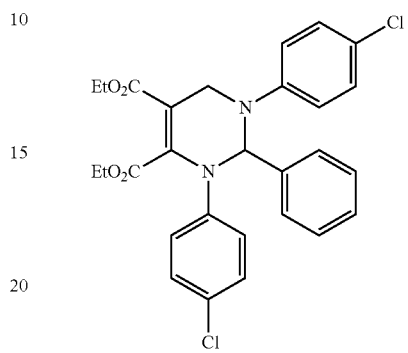

diethyl 1,3-bis(4-chlorophenyl)-1,2,3,6-tetrahydro-2-phenylpyrimidine-4,5-dicarboxylate, Compound 4; yield=50%, yellow solid, melting point=166.8-167.6° C.; IR (KBr) $v_{max}$=2983, 2357, 1740, 1697, 1601, 1492, 1232, 1104, 1007, 825, 756, 700 cm$^{-1}$; $^1$H NMR (400 MHz, CDCl$_3$): (δ=7.63-6.86 (m, 13H), 5.60 (s, 1H), 4.21 (d, J=18.0 Hz, 1H), 4.15-4.11 (m, 4H), 3.56 (d, J=18.0 Hz, 1H), 1.22 (t, J=7.2 Hz, 3H), 1.10 (t, J=7.2 Hz, 3H) ppm; $^{13}$C NMR (101 MHz, CDCl$_3$): δ=165.19, 164.00, 148.07, 144.30, 142.93, 137.71, 131.71, 129.36, 129.26, 128.67, 126.81, 126.66, 125.42, 120.45, 102.21, 80.31, 61.94, 60.41, 42.57, 14.20, 13.68 ppm; MS (ESI): m/z 525 (M+H$^1$, 45), 310 (100); Anal. Calcd for C$_{28}$H$_{26}$Cl$_2$N$_2$O$_4$: C, 64.01; H, 4.99; N, 5.33. Found: C, 64.23; H, 4.83; N, 5.45.

Example 5

(1) 1 mmol (170 mg) of diethyl acetylenedicarboxylate and 1 mmol (170 mg) of p-bromoaniline were successively added into 3 mL of methanol, which was then stirred at room temperature by 30 min.
(2) 1.5 mmol (285 mg) of p-bromoaniline, 1.2 mmol (120 mg) of formaldehyde (30%) and 5 mmol (300 mg) acetic acid were added into 5 mL of methanol, which was then stirred at room temperature by 10 min.
(3) The solutions obtained by (1) and (2) were mixed, and then added with 1.5 mmol (159 mg) of benzaldehyde at room temperature. After 36 h of reaction, 20 mL of saturated aqueous sodium chloride was added. Then extraction with 20 mL of dichloromethane was repeated 3 times. The dichloromethane solutions were mixed and then extracted with 20 mL of saturated aqueous sodium chloride by 3 times. The resulting dichloromethane solution was dried with magnesium sulfate, and then subjected to distillation under reduced pressure to remove the solvent. The product was purified by preparative layer chromatography, using n-hexane+ethyl acetate (10:1) as the developing agent and ethyl acetate as the eluting agent. Vacuum rotary evaporation was performed to remove the solvent and 318 mg of Compound 5 was obtained.

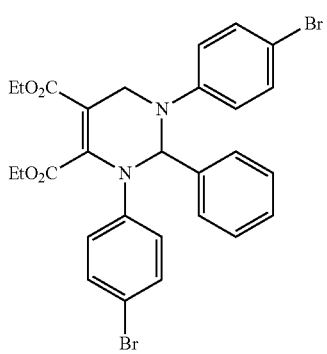 [SMILES: CCOC(=O)C1=C(C(=O)OCC)N(c2ccc(Br)cc2)C(c2ccccc2)N(c2ccc(Br)cc2)C1]
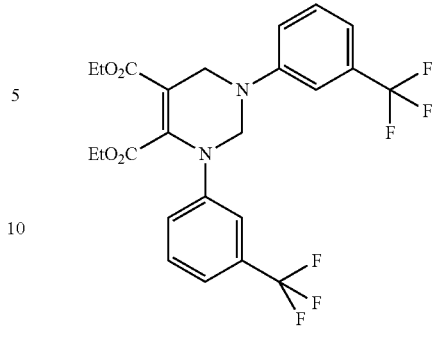

diethyl 1,3-bis(4-bromophenyl)-1,2,3,6-tetrahydro-2-phenylpyrimidine-4,5-dicarboxylate, Compound 5; yield=52%, yellow solid, melting point=154.6-155.4° C.; IR (KBr): $v_{max}$=2982, 2360, 1738, 1696, 1597, 1490, 1232, 1109, 1005, 820, 756, 700 cm$^{-1}$; $^1$HNMR (400 MHz, CDCl$_3$): δ=7.62-7.31 (m, 9H), 6.90-6.81 (m, 4H), 6.01 (s, 1H), 4.21 (d, J=18.0 Hz, 1H), 4.15-4.10 (m, 4H), 3.55 (d, J=18.0 Hz, 1H), 1.22 (t, J=7.2 Hz, 3H), 1.11 (t, J=7.2 Hz, 3H) ppm; $^{13}$C NMR (101 MHz, CDCl$_3$): δ=165.12, 163.97, 148.49, 144.10, 143.45, 137.66, 132.34, 132.30, 129.27, 128.68, 126.79, 125.61, 120.68, 119.50, 114.01, 102.52, 79.92, 61.95, 60.42, 42.60, 14.19, 13.68 ppm; MS (ESI): m/z 613 (M+H$^+$, 15), 615 (M+H$^+$, 31), 354 (90), 356 (100); Anal. Calcd for C$_{28}$H$_{26}$Br$_2$N$_2$O$_4$: C, 54.74; H, 4.27; N, 4.56. Found: C, 54.81; H, 4.35; N, 4.61.

diethyl 1,3-bis(3-(trifluoromethyl)phenyl)-1,2,3,6-tetrahydro-2-phenylpyrimidine-4,5-dicarboxylate, Compound 6; yield=50%, white solid, melting point=104.4-105.2° C.; IR (KBr): $v_{max}$=2986, 2357, 1741, 1700, 1600, 1499, 1234, 1125, 866, 758, 695 cm$^{-1}$; $^1$H NMR (400 MHz, CDCl$_3$): δ=7.64-7.14 (m, 13H), 6.14 (s, 1H), 4.33 (d, J=18.4 Hz, 1H), 4.16-4.10 (m, 4H), 3.66 (d, J=18.4 Hz, 1H), 1.23 (t, J=7.2 Hz, 3H), 1.12 (t, J=7.2 Hz, 3H) ppm; $^{13}$C NMR (101 MHz, CDCl$_3$): δ=164.90, 163.98, 149.65, 144.95, 143.46, 137.25, 130.15, 130.03, 129.40, 128.84, 126.73, 126.54, 122.53, 121.87, 120.41, 118.19, 115.25, 104.65, 79.21, 62.13, 60.61, 43.29, 14.17, 13.42 ppm; MS (ESI): m/z 593 (M+H$^+$, 45), 344 (100); Anal. Calcd for C$_{30}$H$_{26}$F$_6$N$_2$O$_4$: C, 60.81; H, 4.42; N, 4.73. Found: C, 60.98; H, 4.53; N, 4.61.

Example 6

(1) 1 mmol (170 mg) of diethyl acetylenedicarboxylate and 1 mmol (161 mg) of m-trifluoromethylaniline were successively added into 1 mL of methanol, which was then stirred at room temperature by 60 min.

(2) 3 mmol (483 mg) of m-trifluoromethylaniline, 1.4 mmol (112 mg) of formaldehyde (30%) and 4 mmol (240 mg) of acetic acid were added into 5 mL of methanol, which was then stirred at room temperature by 10 min.

(3) The solutions obtained by (1) and (2) were mixed, and then added with 1.5 mmol (159 mg) of benzaldehyde and 0.2 mmol (12 mg) of urea at room temperature. After 48 h of reaction, 20 mL of saturated aqueous sodium chloride was added. Then extraction with 20 mL of dichloromethane was repeated 3 times. The dichloromethane solutions were mixed and then extracted with 20 mL of saturated aqueous sodium chloride by 3 times. The resulting dichloromethane solution was dried with magnesium sulfate, and then subjected to distillation under reduced pressure to remove the solvent. The product was purified by preparative layer chromatography, using n-hexane+ethyl acetate (10:1) as the developing agent and ethyl acetate as the eluting agent. Vacuum rotary evaporation was performed to remove the solvent and 291 mg of Compound 6 was obtained.

Example 7

(1) 1 mmol (170 mg) of diethyl acetylenedicarboxylate and 1 mmol (107 mg) of m-toluidine were successively added into 1 mL of methanol, which was then stirred at room temperature by 60 min.

(2) 3 mmol (321 mg) of m-toluidine, 1.4 mmol (112 mg) of formaldehyde (30%) and 0.1 mmol (9.8 mg) sulfuric acid were added into 5 mL of methanol, which was then stirred at room temperature by 10 min.

(3) The solutions obtained by (1) and (2) were mixed, and then added with 1.5 mmol (159 mg) of benzaldehyde and 0.2 mmol (12 mg) of urea at room temperature. After 48 h of reaction, 20 mL of saturated aqueous sodium chloride was added. Then extraction with 20 mL of dichloromethane was repeated 3 times. The dichloromethane solutions were mixed and then extracted with 20 mL of saturated aqueous sodium chloride by 3 times. The resulting dichloromethane solution was dried with magnesium sulfate, and then subjected to distillation under reduced pressure to remove the solvent. The product was purified by preparative layer chromatography, using n-hexane+ethyl acetate (10:1) as the developing agent and ethyl acetate as the eluting agent. Vacuum rotary evaporation was performed to remove the solvent and 291 mg of Compound 7 was obtained.

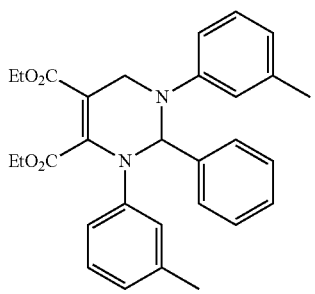 [SMILES: CCOC(=O)C1=C(C(=O)OCC)N(c2cccc(C)c2)C(c2ccccc2)N(c2cccc(C)c2)C1]

diethyl 1,3-bis(3-methylphenyl)-1,2,3,6-tetrahydro-2-phenylpyrimidine-4,5-dicarboxylate, Compound 7; yield=46%, yellow solid, melting point=100.0-100.8° C.; IR (KBr): $\nu_{max}$=2980, 1740, 1698, 1582, 1492, 1249, 1178, 1108, 759, 698 cm$^{-1}$; $^1$H NMR (400 MHz, CDCl$_3$): δ=7.65-6.72 (m, 13H), 6.10 (s, 1H), 4.29 (d, J=17.6 Hz, 1H), 4.15-4.07 (m, 4H), 3.57 (d, J=17.6 Hz, 1H), 1.21 (t, J=7.2 Hz, 3H), 1.07 (t, J=7.2 Hz, 3H) ppm; $^{13}$C NMR (101 MHz, CDCl$_3$): δ=165.46, 164.42, 149.56, 144.81, 144.45, 139.05, 138.60, 129.14, 129.04, 128.88, 128.25, 127.03, 126.82, 124.90, 121.99, 121.40, 119.45, 115.63, 101.85, 78.90, 61.60, 60.12, 43.10, 21.69, 21.31, 14.24, 13.62 ppm; MS (ESI): m/z 485 (M+H$^+$, 50), 290 (100); Anal. Calcd for C$_{30}$H$_{32}$N$_2$O$_4$: C, 74.36; H, 6.66; N, 5.78. Found: C, 74.13; H, 6.69; N, 5.84.

The synthesis methods in the following examples are almost the same as that in Example 6, except that corresponding materials were replaced.

Example 8

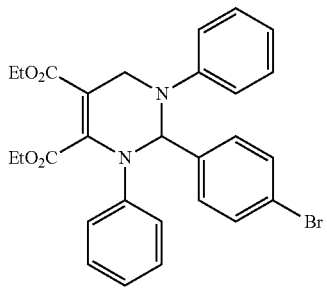 [SMILES: CCOC(=O)C1=C(C(=O)OCC)N(c2ccccc2)C(c2ccc(Br)cc2)N(c2ccccc2)C1]

diethyl 2-(4-bromophenyl)-1,2,3,6-tetrahydro-1,3-diphenylpyrimidine-4,5-dicarboxylate, Compound 8; yield=31%, yellow solid, melting point=162.4-164.6° C.; IR (KBr): $\nu_{max}$=2981, 2352, 1739, 1697, 1592, 1495, 1372, 1293, 1236, 1107, 1009, 910, 747, 696 cm$^{-1}$; $^1$H NMR (400 MHz, CDCl$_3$): δ=7.59-6.92 (m, 14H), 6.04 (s, 1H), 4.29 (d, J=17.6 Hz, 1H), 4.14-4.08 (m, 4H), 3.56 (d, J=17.6 Hz, 1H), 1.23 (t, J=7.2 Hz, 3H), 1.03 (t, J=7.2 Hz, 3H) ppm; $^{13}$C NMR (101 MHz, CDCl$_3$): δ=165.28, 164.15, 149.32, 144.61, 144.24, 137.55, 132.27, 129.40, 129.20, 128.89, 126.17, 124.22, 122.49, 121.68, 118.99, 102.05, 79.30, 61.75, 60.29, 42.75, 14.22, 13.58 ppm; MS (ESI): m/z 535 (M+H$^+$, 49), 537 (M+H$^+$, 49), 276 (100); Anal. Calcd for C$_{28}$H$_{27}$BrN$_2$O$_4$: C, 62.81; H, 5.08; N, 5.23. Found: C, 62.93; H, 5.18; N, 5.16.

Example 9

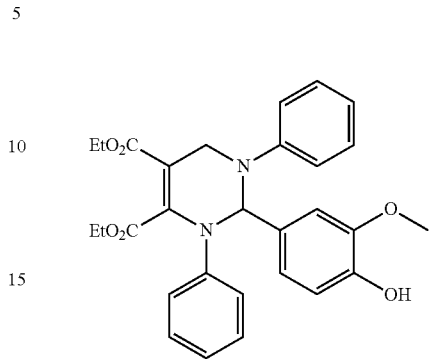

diethyl 1,2,3,6-tetrahydro-2-(4-hydroxy-3-methoxyphenyl)-1,3-diphenylpyrimidine-4,5-dicarboxylate, Compound 9; yield=53%, yellow solid, melting point=164.1-164.6° C.; IR (KBr): $\nu_{max}$=2981, 2360, 1735, 1697, 1579, 1496, 1282, 1235, 1109, 763, 696 cm$^1$; $^1$H NMR (400 MHz, CDCl$_3$): δ=7.26-6.89 (m, 13H), 6.08 (s, 1H), 5.69 (s, 1H), 4.28 (d, J=17.6 Hz, 1H), 4.14-4.05 (m, 4H), 3.88 (s, 3H), 3.63 (d, J=17.6 Hz, 1H), 1.22 (t, J=7.2 Hz, 3H), 1.05 (t, J=7.2 Hz, 3H) ppm; $^{13}$C NMR (101 MHz, CDCl$_3$): δ=165.39, 164.37, 149.51, 146.90, 145.53, 144.53, 144.48, 130.23, 129.32, 129.13, 125.84, 123.86, 121.35, 119.90, 118.88, 114.85, 109.52, 102.26, 79.24, 61.65, 60.18, 56.02, 53.45, 42.85, 14.23, 13.63 ppm; MS (ESI): m/z 503 (M+H$^+$, 34), 276(30), 228 (100); Anal. Calcd for C$_{29}$H$_{30}$N$_2$O$_6$: C, 69.31; H, 6.02; N, 5.57. Found: C, 69.24; H, 6.16; N, 5.45.

Example 10

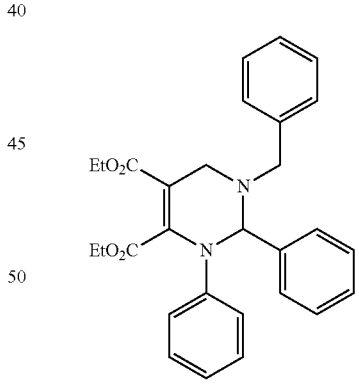

diethyl 1-benzyl-1,2,3,6-tetrahydro-2,3-diphenylpyrimidine-4,5-dicarboxylate, Compound 10; yield=37%, white solid, melting point=100.0-100.8° C.; IR (KBr): $\nu_{max}$=3061, 3030, 2980, 2930, 2362, 1736, 1697, 1630, 1578, 1496, 1283, 1104, 1056, 752, 698 cm$^{-1}$; $^1$H NMR (400 MHz, CDCl$_3$): δ=7.62-7.15 (m, 15H), 5.22 (s, 1H), 4.24-4.08 (m, 4H), 3.95 (s, 2H), 3.56 (d, J=17.6 Hz, 1H), 3.34 (d, J=17.6 Hz, 1H), 1.22 (t, J=7.2 Hz, 3H), 1.13 (t, J=7.2 Hz, 3H) ppm; $^{13}$C NMR (101 MHz, CDCl$_3$) δ=166.16, 164.52, 144.78, 143.92, 129.11, 128.96, 128.81, 128.35, 128.07, 127.33, 127.12, 125.72, 123.89, 99.89, 79.28, 61.73, 60.01, 57.60, 44.12, 14.22, 13.66 ppm;

MS (ESI): m/z 471 (M+H$^+$, 100); Anal. Calcd for C$_{29}$H$_{30}$N$_2$O$_4$: C, 74.02; H, 6.43; N, 5.95. Found: C, 74.31; H, 6.54; N, 5.83.

Example 11

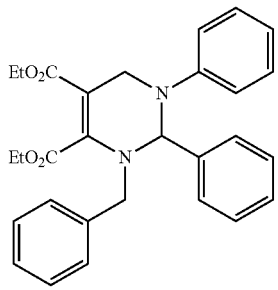 [SMILES: CCOC(=O)C1=C(C(=O)OCC)N(Cc2ccccc2)C(c2ccccc2)N(c2ccccc2)C1]

diethyl 3-benzyl-1,2,3,6-tetrahydro-1,2-diphenylpyrimidine-4,5-dicarboxylate, Compound 11; yield=21%, white solid, melting point=102.4-103.4° C.; IR (KBr): ν$_{max}$=3061, 3029, 2980, 2935, 2903, 1737, 1692, 1593, 1496, 1452, 1367, 1284, 1223, 1147, 1108, 1032, 749, 697 cm$^{-1}$; $^1$H NMR (400 MHz, CDCl$_3$): δ=7.36-7.25 (m, 4H), 7.19 (s, 1H), 7.06 (m, 5H), 6.92 (m, 5H), 5.62 (s, 1H), 4.43 (d, J=16.0 Hz, 1H), 4.33-4.22 (m, 2H), 4.10-4.02 (m, 4H), 3.43 (d, J=16.8 Hz, 1H), 1.21-1.15 (m, 6H) ppm; $^{13}$C NMR (101 MHz, CDCl$_3$): δ=165.69, 165.05, 149.11, 148.47, 137.40, 135.91, 129.19, 128.92, 128.47, 128.36, 127.72, 127.69, 126.69, 121.16, 118.84, 93.52, 75.64, 62.14, 59.82, 53.81, 40.16, 14.40, 13.86 ppm; MS (ESI): m/z 471 (M+H$^+$, 45); Anal. Calcd for C$_{29}$H$_{30}$N$_2$O$_4$: C, 74.02; H, 6.43; N, 5.95. Found: C, 74.13; H, 6.33; N, 5.79.

Example 12

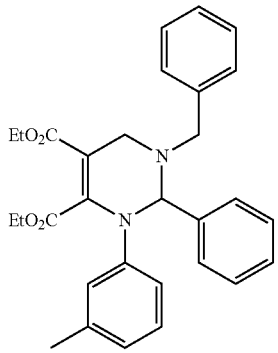 [SMILES: CCOC(=O)C1=C(C(=O)OCC)N(c2cccc(C)c2)C(c2ccccc2)N(Cc2ccccc2)C1]

diethyl 1-benzyl-1,2,3,6-tetrahydro-3-(3-methylphenyl)-2-phenylpyrimidine-4,5-dicarboxylate, Compound 12; yield=38%, yellow oil; IR (KBr): ν$_{max}$=3061, 3029, 2978, 2852, 1738, 1697, 1581, 1492, 1450, 1366, 1249, 1217, 1177, 1105, 1061, 781, 699 cm$^{-1}$; $^1$H NMR (400 MHz, CDCl$_3$): δ=7.52-6.85 (m, 14H), 5.12 (s, 1H), 4.14-4.07 (m, 2H), 4.00 (q, J=7.2 Hz, 2H), 3.83 (s, 2H), 3.43 (d, J=18.0 Hz, 1H), 3.20 (d, J=18.0 Hz, 1H), 2.18 (s, 3H), 1.10 (t, J=7.2 Hz, 3H), 1.05 (t, J=7.2 Hz, 3H) ppm; $^{13}$C NMR (101 MHz, CDCl$_3$): δ=166.22, 164.64, 144.77, 143.97, 139.41, 139.04, 138.32, 128.95, 128.87, 128.80, 128.32, 128.00, 127.28, 127.14, 126.52, 124.38, 120.96, 99.85, 79.42, 61.69, 59.98, 57.57, 44.02, 21.35, 14.22, 13.69 ppm; MS (ESI): m/z 485 (M+H$^+$, 100); Anal. Calcd for C$_{30}$H$_{32}$N$_2$O$_4$: C, 74.36; H, 6.66; N, 5.78. Found: C, 74.16; H, 6.57; N, 5.69.

Example 13

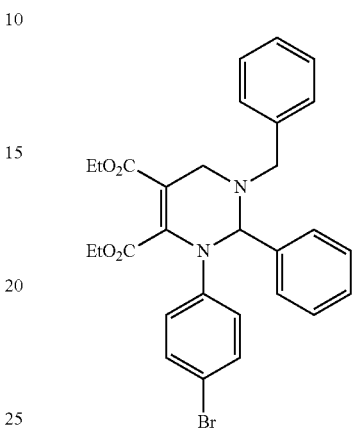

diethyl 1-benzyl-3-(4-bromophenyl)-1,2,3,6-tetrahydro-2-phenylpyrimidine-4,5-dicarboxylate, Compound 13; yield=29%, white solid, melting point=119.9-121.4° C.; IR (KBr): ν$_{max}$=3278, 2929, 2358, 1690, 1621, 1548, 1193, 1070, 737, 670 cm$^{-1}$; $^1$H NMR (400 MHz, CDCl$_3$): δ=7.59-7.03 (m, 14H), 5.17 (s, 1H), 4.25-4.22 (m, 2H), 4.13-4.08 (m, 2H), 3.95 (d, J=13.6 Hz, 1H), 3.89 (d, J=13.6 Hz, 1H), 3.55 (d, J=18.4 Hz, 2H), 3.33 (d, J=18.4 Hz, 2H), 1.23-1.19 (m, 6H) ppm; $^{13}$C NMR (101 MHz, CDCl$_3$): δ=165.97, 164.38, 144.00, 143.06, 138.90, 137.92, 132.19, 128.93, 128.88, 128.44, 128.22, 127.46, 126.99, 125.03, 118.69, 101.37, 79.18, 61.93, 60.17, 57.64, 44.21, 14.19, 13.76 ppm; MS (ESI): m/z 549 (M+H$^+$, 80), 551(M+H$^+$, 100); Anal. Calcd for C$_{29}$H$_{29}$BrN$_2$O$_4$: C, 63.39; H, 5.32; N, 5.10. Found: C, 63.51; H, 5.42; N, 5.0.

Example 14

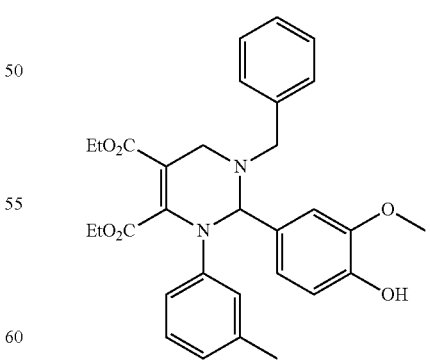

diethyl 1-benzyl-1,2,3,6-tetrahydro-2-(4-hydroxy-3-methoxyphenyl)-3-m-tolylpyrimidine-4,5-dicarboxylate, Compound 14; yield=31% yellow solid, melting point=170.3-171.6° C.; IR (KBr): =3434, 2980, 2358, 1734, 1696, 1581, 1515, 1251, 1107, 736, 670 cm⁻¹; ¹H NMR (400 MHz, CDCl₃): δ=7.26-6.93 (m, 12H), 5.65 (s, 1H), 5.16 (s, 1H), 4.19-4.04 (m, 4H), 3.88 (s, 3H), 3.87 (s, 2H), 3.48 (d, J=18.0 Hz, 1H), 3.31 (d, J=18.0 Hz, 1H), 2.26 (s, 3H), 1.20-1.12 (m, 6H) ppm; ¹³C NMR (101 MHz, CDCl₃) δ=166.13, 164.74, 146.65, 145.22, 144.95, 143.50, 139.06, 138.39, 131.30, 128.89, 128.29, 127.23, 126.24, 123.71, 120.28, 120.01, 114.71, 109.77, 100.97, 79.11, 61.65, 59.99, 57.48, 55.96, 44.08, 21.37, 14.22, 13.74 ppm; MS (ESI): m/z 531(M+H⁺, 41), 242 (100); Anal. Calcd for $C_{31}H_{34}N_2O_6$: C, 70.17; H, 6.46; N, 5.28. Found: C, 70.23; H, 6.38; N, 5.19.

Example 15

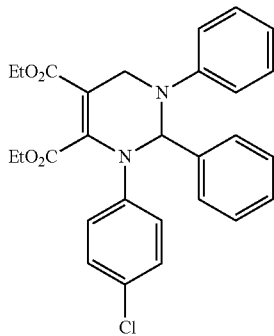 [SMILES: CCOC(=O)C1=C(C(=O)OCC)N(c2ccc(Cl)cc2)C(c2ccccc2)N(c2ccccc2)C1]

diethyl 3-(4-chlorophenyl)-1,2,3,6-tetrahydro-1,2-diphenylpyrimidine-4,5-dicarboxylate, Compound 15; yield=47%, yellow solid, melting point=141.7-142.3° C.; IR (KBr): $v_{max}$=2981, 1738, 1698, 1599, 1492, 1237, 1102, 828, 750, 697 cm⁻¹; ¹H NMR (400 MHz, CDCl₃): δ=7.66-6.86 (m, 14H), 6.06 (s, 1H), 4.28 (d, J=18.0 Hz, 1H), 4.14-4.08 (m, 4H), 3.58 (d, J=18.0 Hz, 1H), 1.22 (t, J=7.2 Hz, 3H), 1.09 (t, J=7.2 Hz, 3H) ppm; ¹³C NMR (101 MHz, CDCl₃): δ=165.30, 164.13, 149.45, 144.29, 143.13, 138.10, 131.49, 129.42, 129.23, 129.19, 128.50, 126.89, 125.48, 121.71, 119.06, 102.67, 80.25, 61.84, 60.31, 42.55, 14.21, 13.68 ppm; MS (ESI): m/z 491 (M+H⁺, 56), 276 (100); Anal. Calcd for $C_{28}H_{27}ClN_2O_4$: C, 68.50; H, 5.54; N, 5.71. Found: C, 68.39; H, 5.50; N, 5.85.

Example 16

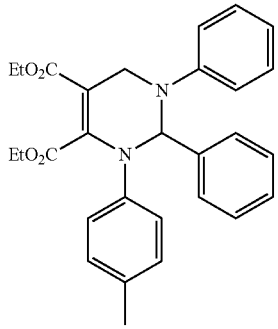 [SMILES: CCOC(=O)C1=C(C(=O)OCC)N(c2ccc(C)cc2)C(c2ccccc2)N(c2ccccc2)C1]

diethyl 3-(4-methylphenyl)-1,2,3,6-tetrahydro-1,2-diphenylpyrimidine-4,5-dicarboxylate, Compound 16; yield=37%, yellow solid, melting point=123.9-125.2° C.; IR (KBr): $v_{max}$=3073, 2357, 1742, 1699, 1508, 1234, 1107, 911, 757, 683 cm⁻¹; ¹H NMR (400 MHz, CDCl₃): δ=7.71-6.87 (m, 14H), 6.11 (s, 1H), 4.31 (d, J=17.6 Hz, 1H), 4.18-4.10 (m, 4H), 3.61 (d, J=17.6 Hz, 1H), 2.29 (s, 3H), 1.25 (t, J=7.2 Hz, 3H), 1.09 (t, J=7.2 Hz, 3H) ppm; NMR (101 MHz, CDCl₃) δ=165.52, 164.34, 149.63, 145.40, 141.78, 138.55, 136.07, 129.66, 129.35, 129.08, 129.03, 128.30, 127.02, 124.65, 124.45, 121.39, 119.03, 118.99, 100.34, 79.91, 61.61, 60.09, 42.48, 20.95, 14.25, 13.63 ppm; MS (ESI): m/z 471 (M+H⁺, 48), 276 (100); Anal. Calcd for $C_{29}H_{1L}N_2O_4$: C, 74.02; H, 6.43; N, 5.95. Found: C, 74.29; H, 6.27; N, 5.78.

Example 17

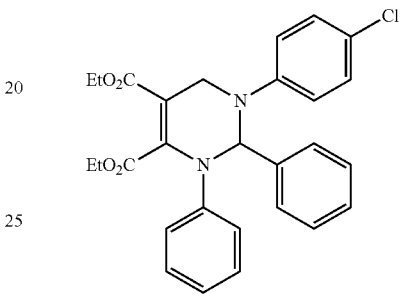

diethyl 1-(4-chlorophenyl)-1,2,3,6-tetrahydro-2,3-diphenylpyrimidine-4,5-dicarboxylate, Compound 17; yield=53%, white solid, melting point=139.3-139.9° C.; IR (KBr): $v_{max}$=3115, 2359, 1702, 1515, 966, 676 cm⁻¹; ¹H NMR (400 MHz, CDCl₃): δ=7.47-6.88 (m, 14H), 6.02 (s, 1H), 4.23 (d, J=18.0 Hz, 1H), 4.17-4.11 (m, 4H), 3.58 (d, J=18.0 Hz, 1H), 1.25 (t, J=7.2 Hz, 3H), 1.12 (t, J=7.2 Hz, 3H) ppm; ¹³C NMR (101 MHz, CDCl₃): δ=165.17, 163.98, 148.07, 142.94, 137.72, 131.72, 129.36, 129.25, 128.65, 126.80, 125.43, 120.43, 102.22, 80.32, 61.92, 60.40, 42.56, 14.19, 13.66 ppm; MS (ESI): m/z 491 (M+H⁺, 100), 310 (80); Anal. Calcd for $C_{28}H_{27}ClN_2O_4$: C, 68.50; H, 5.54; N, 5.71. Found: C, 68.30; H, 5.51; N, 5.83.

Example 18

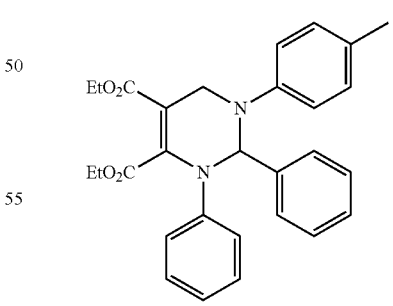

diethyl 1-(4-methylphenyl)-1, 2,3,6-tetrahydro-2,3-diphenylpyrimidine-4,5-dicarboxylate, Compound 18; yield=36%, white solid, melting point=131.1-132.2° C.; IR (KBr): $v_{max}$=2984, 2358, 1742, 1698, 1508, 1232, 1108, 1008, 756, 683 cm⁻¹; ¹H NMR (400 MHz, CDCl₃): δ=7.67-6.84 (m, 14H), 6.04 (s, 1H), 4.23 (d, J=18.0 Hz, 1H), 4.13-4.08 (m, 4H), 3.57 (d, J=18.0 Hz, 1H), 2.26 (s, 3H), 1.21 (t, J=7.2 Hz, 3H), 1.03 (t, J=7.2 Hz, 3H) ppm; $^{13}$C NMR (101 MHz, CDCl$_3$): δ=165.53, 164.29, 147.32, 145.01, 144.45, 138.60, 130.98, 129.84, 129.62, 129.06, 129.03, 128.98, 128.29, 127.05, 126.01, 124.69, 124.48, 119.27, 101.27, 80.18, 61.63, 60.11, 60.02, 42.83, 20.58, 14.22, 13.58 ppm; MS (ESI): m/z 471 (M+H$^+$, 90), 290 (100); Anal. Calcd for C$_{29}$H$_{30}$N$_2$O$_4$: C, 74.02; H, 6.43; N, 5.95. Found: C, 74.32; H, 6.57; N, 5.76.

Example 19

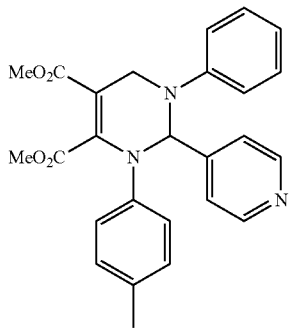 [SMILES: COC(=O)C1=C(C(=O)OC)N(c2ccc(C)cc2)C(c2ccncc2)N(c2ccccc2)C1]

dimethyl 1,2,3,6-tetrahydro-1-phenyl-2-(pyridin-4-yl)-3-p-tolylpyrimidine-4,5-dicarboxylate, Compound 35; yield=11%, white solid, melting point=202.2-203.1° C.; $^1$H NMR (600 MHz, CDCl$_3$): δ=8.71 (d, J=5.2 Hz, 2H), 7.62 (d, J=5.6 Hz, 2H), 7.24-6.90 (m, 9H), 5.99 (s, 1H), 4.23 (d, J=18.0 Hz, 1H), 3.67 (s, 3H), 3.66 (s, 3H), 3.52 (d, J=18.0 Hz, 1H), 2.27 (s, 3H) ppm; $^{13}$C NMR (151 MHz, CDCl$_3$): δ=165.54, 164.64, 150.46, 147.83, 146.72, 144.56, 143.99, 131.66, 129.98, 129.36, 126.30, 123.86, 122.10, 119.16, 102.52, 79.19, 52.66, 51.57, 43.07, 20.54. ppm; MS (ESI): m/z 444 (M+H$^+$, 100), 248(30), 197 (80); Anal. Calcd for C$_{26}$H$_{25}$N$_3$O$_4$: C, 70.41; H, 5.68; N, 9.47. Found: C, 70.53; H, 5.54; N, 9.22.

Example 20

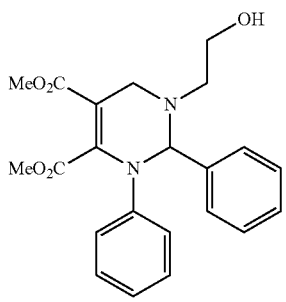 [SMILES: COC(=O)C1=C(C(=O)OC)N(c2ccccc2)C(c2ccccc2)N(CCO)C1]

dimethyl 1,2,3,6-tetrahydro-1-(2-hydroxyethyl)-2,3-diphenylpyrimidine-4,5-dicarboxylate, Compound 20; yield=23%, white solid, melting point=49.9-50.8° C.; IR (KBr): v$_{max}$=3510, 2948, 2353, 1741, 1695, 1583, 1495, 1236, 1111, 756, 697 cm$^{-1}$; $^1$H NMR (400 MHz, CDCl$_3$): δ=7.56-7.11 (m, 10H), 5.31 (s, 1H), 3.77-3.75 (m, 1H), 3.68 (s, 3H), 3.66 (b, 1H), 3.63 (s, 3H), 3.50 (d, J=18.0 Hz, 1H), 3.18 (d, J=18.0 Hz, 1H), 3.97-3.91 (m, 2H), 2.58 (s, 1H) ppm; $^{13}$C NMR (101 MHz, CDCl$_3$): δ=166.39, 164.82, 144.45, 144.34, 138.48, 129.36, 129.01, 128.44, 126.97, 126.29, 124.01, 98.66, 81.82, 59.14, 55.04, 52.65, 51.38, 42.52 ppm; MS (ESI): m/z 397 (M+H$^+$, 100), 419 (M+Na$^+$, 47); Anal. Calcd for C$_{22}$H$_{24}$N$_2$O$_5$: C, 66.65; H, 6.10; N, 7.07. Found: C, 66.45; H, 6.21; N, 7.12.

Example 21

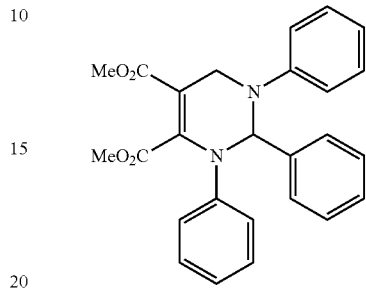

dimethyl 1,2,3,6-tetrahydro-1,2,3-triphenylpyrimidine-4,5-dicarboxylate, Compound 21; yield=61%, yellow solid, melting point=145.8-146.5° C.; IR (KBr): v$_{max}$=2950, 2356, 1743, 1699, 1589, 1496, 1234, 1112, 917, 756, 696 cm$^{-1}$; $^1$H NMR (400 MHz, CDCl$_3$): δ=7.67-6.91 (m, 15H), 6.12 (s, 1H), 4.28 (d, J=17.6 Hz, 1H), 3.66 (s, 3H), 3.64 (s, 3H), 3.59 (d, J=17.6 Hz, 1H) ppm; $^{13}$C NMR (101 MHz, CDCl$_3$) δ=165.88, 164.89, 149.47, 145.00, 144.33, 138.28, 129.37, 129.23, 129.12, 128.43, 126.96, 126.12, 124.04, 121.58, 119.01, 101.33, 79.96, 52.60, 51.48, 42.57 ppm; MS (ESI): m/z 429 (M+H$^+$, 41), 248 (100); Anal. Calcd for C$_{26}$H$_{24}$N$_2$O$_4$: C, 72.88; H, 5.65; N, 6.54. Found: C, 72.97; H, 5.49; N, 6.61.

Example 22

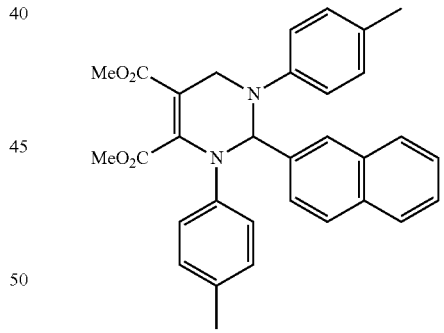

dimethyl 1,2,3,6-tetrahydro-2-(naphthalen-2-yl)-1,3-dip-tolylpyrimidine-4,5-dicarboxylate, Compound 36; yield=29%, white solid, melting point=158.0-159.0° C.; IR (KBr): v$_{max}$=3027, 2948, 2920, 2860, 1742, 1701, 1592, 1511, 1434, 1366, 1236, 1111, 1064, 818, 739, 480 cm$^{-1}$; $^1$H NMR (600 MHz, CDCl$_3$): δ=8.19 (s, 1H), 7.96-7.88 (m, 3H), 7.76 (dd, J=8.5, 1.2 Hz, 1H), 7.55 (dd, J=6.2, 3.2 Hz, 2H), 7.11 (d, J=8.4 Hz, 2H), 7.03 (dd, J=14.8, 8.4 Hz, 4H), 6.92 (d, J=8.3 Hz, 2H), 6.19 (s, 1H), 4.28 (d, J=17.9 Hz, 1H), 3.73 (s, 3H), 3.65 (s, 3H), 3.62 (d, J=17.9 Hz, 1H), 2.32 (s, 3H), 2.29 (s, 3H) ppm; $^{13}$C NMR (151 MHz, CDCl$_3$): δ=165.83, 164.94, 147.27, 145.46, 141.70, 135.95, 135.72, 133.32, 133.22, 131.05, 129.81, 129.72, 128.93, 128.59, 127.55, 126.44, 126.37, 126.19, 124.61, 124.18, 119.36, 100.04, 80.38, 52.46, 51.23, 42.71, 20.85, 20.52 ppm; MS (ESI): m/z 507 (M+H$^+$, 28), 262(55), 246 (100); Anal. Calcd for C$_{32}$H$_{30}$N$_2$O$_4$: C, 75.87; H, 5.97; N, 5.53. Found: C, 75.61; H, 5.83; N, 5.67.

Example 23

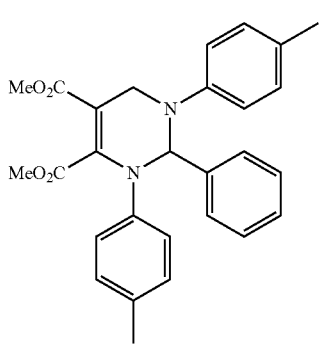 [SMILES: COC(=O)C1=C(C(=O)OC)N(c2ccc(C)cc2)C(c2ccccc2)N(c2ccc(C)cc2)C1]

dimthyl 1,3-bis(4-methylphenyl)-1,2,3,6-tetrahydro-2-phenylpyrimidine-4,5-dicarboxylate, Compound 23; yield=63%, yellow solid, melting point=164.1-164.6° C.; IR (KBr): $\nu_{max}$=3688, 3031, 1742, 1699, 1593, 1510, 1239, 1110, 1064, 913, 821, 747 cm$^{-1}$; $^1$H NMR (400 MHz, CDCl$_3$): δ=7.65-6.81 (m, 13H), 6.00 (s, 1H), 4.20 (d, J=17.6 Hz, 1H), 3.65 (s, 6H), 3.64 (s, 6H), 3.55 (d, J=17.6 Hz, 1H), 2.27 (s, 3H), 2.26 (s, 3H) ppm; $^{13}$C NMR (101 MHz, CDCl$_3$) δ=166.00, 164.98, 147.26, 145.52, 141.69, 138.51, 136.03, 131.04, 129.85, 129.76, 129.02, 128.30, 127.02, 124.31, 119.32, 99.98, 80.34, 52.53, 51.38, 42.57, 20.96, 20.60 ppm; MS (ESI): m/z 457 (M+H$^+$, 34), 262 (100); Anal. Calcd for C$_{28}$H$_{28}$N$_2$O$_4$: C, 73.66; H, 6.18; N, 6.14. Found: C, 73.51; H, 6.23; N, 6.25.

Example 24

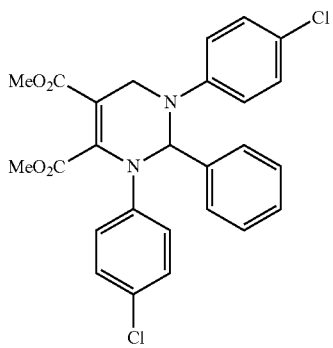 [SMILES: COC(=O)C1=C(C(=O)OC)N(c2ccc(Cl)cc2)C(c2ccccc2)N(c2ccc(Cl)cc2)C1]

dimethyl 1,3-bis(4-chlorophenyl)-1,2,3,6-tetrahydro-2-phenylpyrimidine-4,5-dicarboxylate, Compound 24; yield=55%, light yellow solid, melting point=153.1-153.9° C.; IR (KBr): $\nu_{max}$=3675, 3064, 1741, 1699, 1590, 1493, 1240, 1115, 913, 830, 737, 709 cm$^{-1}$; $^1$H NMR (400 MHz, CDCl$_3$): δ=7.62-6.84 (m, 13H), 6.00 (s, 1H), 4.19 (d, J=18.0 Hz, 1H), 3.68 (s, 3H), 3.66 (s, 3H), 3.56 (d, J=18.0 Hz, 1H) ppm; $^{13}$C NMR (101 MHz, CDCl$_3$): δ=165.59, 164.58, 147.97, 144.37, 142.83, 137.55, 131.79, 129.48, 129.38, 129.29, 128.73, 126.77, 125.11, 120.47, 102.04, 80.43, 52.79, 51.63, 42.49 ppm; MS (ESI): m/z 497 (M+H$^+$, 29), 282 (100); Anal. Calcd for C$_{25}$H$_{27}$N$_3$O$_5$: C$_{26}$H$_{22}$Cl$_2$N$_2$O$_4$: C, 62.79; H, 4.46; N, 5.63. Found: C, 62.87; H, 4.29; N, 5.51.

Example 25

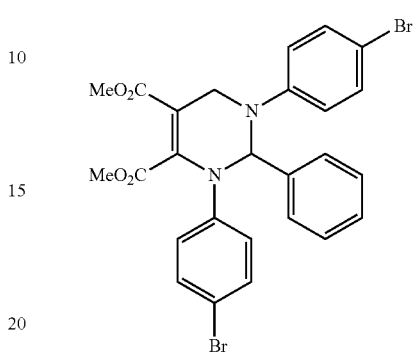

dimethyl 1,3-bis(4-bromophenyl)-1,2,3,6-tetrahydro-2-phenylpyrimidine-4,5-dicarboxylate, Compound 25; yield-47%, light yellow solid, melting point=144.5-145.0° C.; IR (KBr): $\nu_{max}$=2950, 2356, 1741, 1699, 1596, 1490, 1236, 1113, 913, 823, 737, 640 cm$^{-1}$; $^1$H NMR (400 MHz, CDCl$_3$): δ=7.61-6.79 (m, 13H), 6.01 (s, 1H), 4.19 (d, J=18.4 Hz, 1H), 3.68 (s, 3H), 3.66 (s, 3H), 3.56 (d, J=18.4 Hz, 1H) ppm; $^{13}$C NMR (101 MHz, CDCl$_3$): δ=165.54, 164.57, 148.40, 144.19, 143.34, 137.49, 132.47, 132.32, 129.31, 128.75, 126.75, 125.29, 120.72, 119.60, 114.15, 102.32, 80.05, 52.83, 51.65, 42.52 ppm; MS (ESI): m/z 585 (M+H$^+$, 50), 587 (100); Anal. Calcd for C$_{26}$H$_{22}$Br$_2$N$_2$O$_4$: C, 53.27; H, 3.78; N, 4.78. Found: C, 53.43; H, 3.91; N, 4.61.

Example 26

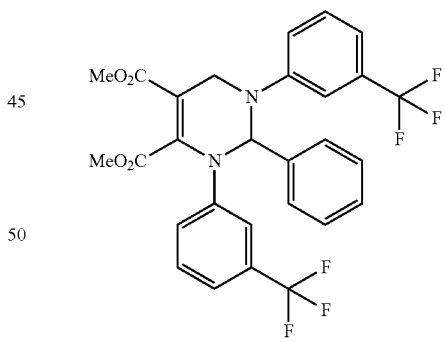

dimethyl 1,3-bis(3-(trifluoromethyl)phenyl)-1,2,3,6-tetrahydro-2-phenylpyrimidine-4,5-dicarboxylate, Compound 26; yield=48%, white solid, melting point=152.3-153.0° C.; IR (KBr): $\nu_{max}$=3687, 2954, 1742, 1704, 1590, 1595, 1235, 1125, 1073, 909, 735, 670, 650 cm$^{-1}$; $^1$H NMR (400 MHz, CDCl$_3$): δ=7.65-7.14 (m, 13H), 6.16 (s, 1H), 4.32 (d, J=18.0 Hz, 1H), 3.70 (s, 3H), 3.68 (s, 3H), 3.67 (d, J=18.0 Hz, 1H) ppm; $^{13}$C NMR (101 MHz, CDCl$_3$): δ=165.29, 164.57, 149.95, 144.84, 143.50, 137.09, 132.04, 131.71, 130.23, 130.07, 129.45, 128.93, 126.69, 126.11, 125.22, 122.51, 121.84, 119.92, 118.32, 118.29, 115.25, 115.21, 104.54, 79.15, 52.75, 51.78, 43.28 ppm; MS (ESI): m/z 565 (M+H+, 32), 316 (100); Anal. Calcd for $C_{28}H_{22}F_6N_2O_4$: C, 59.58; H, 3.93; N, 4.96. Found: C, 59.39; H, 3.81; N, 4.86.

Example 27

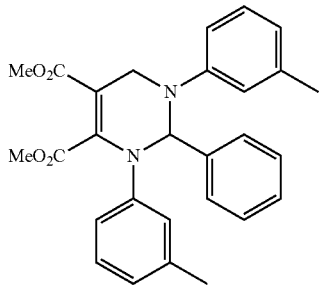 [SMILES: COC(=O)C1=C(C(=O)OC)N(c2cccc(C)c2)C(c2ccccc2)N(c2cccc(C)c2)C1]

dimethyl 1,2,3,6-tetrahydro-2-phenyl-1,3-dim-tolylpyrimidine-4,5-dicarboxylate, Compound 27; yield=52%, yellow solid, melting point=112.9-113.9° C.; IR (KBr): $v_{max}$=2949, 1742, 1702, 1582, 1492, 1251, 1230, 1179, 1112, 758, 698 cm$^{-1}$; $^1$H NMR (400 MHz, CDCl$_3$): δ=7.65-6.72 (m, 13H), 6.11 (s, 1H), 4.26 (d, J=17.6 Hz, 1H), 3.66 (s, 3H), 3.64 (s, 3H), 3.57 (d, J=17.6 Hz, 1H), 2.25 (s, 3H), 2.23 (s, 3H) ppm; $^{13}$C NMR (101 MHz, CDCl$_3$): δ=165.87, 165.05, 149.47, 144.87, 144.39, 139.23, 139.08, 138.44, 129.17, 129.09, 128.95, 128.33, 126.99, 126.89, 124.43, 122.13, 121.03, 119.49, 115.67, 101.75, 79.05, 52.52, 51.44, 43.02, 21.69, 21.35 ppm; MS (ESI): m/z 457 (M+H+, 21), 262 (100); Anal. Calcd for $C_{28}H_{28}N_2O_4$: C, 73.66; H, 6.18; N, 6.14. Found: C, 73.78; H, 6.31; N, 6.09.

Example 28

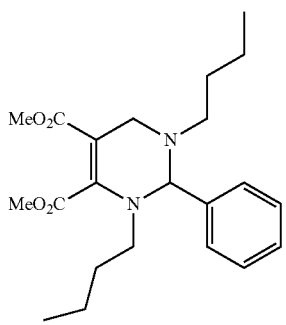 [SMILES: CCCCN1CC(C(=O)OC)=C(C(=O)OC)N(CCCC)C1c1ccccc1]

dimethyl 1,3-dibutyl-1,2,3,6-tetrahydro-2-phenylpyrimidine-4,5-dicarboxylate, Compound 28; yield=41%, yellow oil; IR (KBr): $v_{max}$=2954, 2868, 2358, 1743, 1689, 1577, 1432, 1286, 1140, 1096, 7534, 683 cm$^{-1}$; $^1$HNMR (400 MHz, CDCl$_3$): δ=7.29-7.19 (m, 5H), 4.86 (s, 1H), 3.89 (s, 3H), 3.52 (s, 3H), 3.25 (d, J=16.8 Hz, 1H), 3.18-3.14 (m, 1H), 2.97 (d, J=16.8 Hz, 1H), 2.91-2.88 (m, 2H), 2.57-2.54 (m, 2H), 1.47-1.35 (m, 6H), 1.19-1.14 (m, 2H), 0.90 (t, J=7.2 Hz, 3H), 0.80 (t, J=7.2 Hz, 3H) ppm; $^{13}$C NMR (100 MHz, CDCl$_3$): δ=167.06, 165.57, 147.78, 138.96, 129.46, 128.64, 128.02, 126.81, 115.42, 90.33, 65.57, 52.96, 52.76, 50.90, 50.52, 41.84, 31.87, 30.45, 20.46, 19.86, 14.08, 13.66 ppm; MS (ESI): m/z 389 (M+H+, 100); Anal. Calcd for $C_{22}H_{32}N_2O_4$: C, 68.01; H, 8.30; N, 7.21. Found: C, 68.24; H, 8.19; N, 7.32.

Example 29

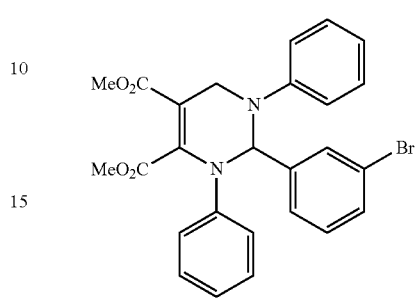

dimethyl 2-(3-bromophenyl)-1,2,3,6-tetrahydro-1,3-diphenylpyrimidine-4,5-dicarboxylate, Compound 29; yield=47%, yellow solid, melting point=142.5-144.3° C.; IR (KBr): $v_{max}$=3036, 2949, 2925, 2853, 1741, 1701, 1592, 1581, 1496, 1472, 1456, 1273, 1113, 1046, 782, 696 cm$^{-1}$; $^1$H NMR (400 MHz, CDCl$_3$): δ=7.80-6.90 (m, 14H), 6.06 (s, 1H), 4.29 (d, J=18.0 Hz, 1H), 3.68 (s, 3H), 3.65 (s, 3H), 3.61 (d, J=18.0 Hz, 1H) ppm; $^{13}$C NMR (101 MHz, CDCl$_3$) δ=165.71, 149.25, 144.12, 140.78, 131.68, 130.74, 130.16, 129.42, 129.31, 126.21, 125.68, 123.87, 123.21, 121.91, 119.15, 101.88, 79.38, 52.66, 51.57, 42.75 ppm; MS (ESI): m/z 507 (M+H+, 100), 509 (100); Anal. Calcd for $C_{26}H_{23}BrN_2O_4$: C, 61.55; H, 4.57; N, 5.52. Found: C, 61.38; H, 4.39; N, 5.61.

Example 30

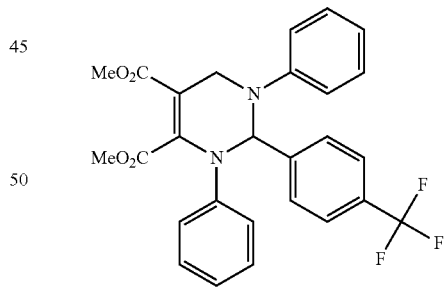

dimethyl-2-(4-(trifluoromethyl)phenyl)-1,2,3,6-tetrahydro-1,3-diphenylpyrimidine-4,5-dicarboxylate, Compound 30; yield=25%, yellow solid, melting point=145.3-146.2° C.; IR (KBr): $v_{max}$=2925, 2852, 2360, 1704, 1596, 1580, 1495, 1435, 1324, 1236, 1111, 1068, 1033, 747, 695 cm$^{-1}$; $^1$H NMR (400 MHz, CDCl$_3$): δ=7.84-6.93 (m, 14H), 6.16 (s, 1H), 4.32 (d, J=18.0 Hz, 1H), 3.70 (s, 3H), 3.68 (s, 3H), 3.56 (d, J=18.0 Hz, 1H) ppm; $^{13}$C NMR (101 MHz, CDCl$_3$): δ=165.63, 164.72, 149.18, 144.64, 144.10, 142.32, 129.47, 129.37, 127.51, 126.29, 126.21, 126.17, 123.84, 121.94, 119.02, 102.20, 79.48, 77.23, 52.68, 51.60, 42.77, 31.60, 22.67, 14.14 ppm; MS (ESI): m/z 497 (M+H⁺, 32), 248 (100); Anal. Calcd for C₂₇H₂₃F₃N₂O₄: C, 65.32; H, 4.67; N, 5.64. Found: C, 65.46; H, 4.58; N, 5.76.

Example 31

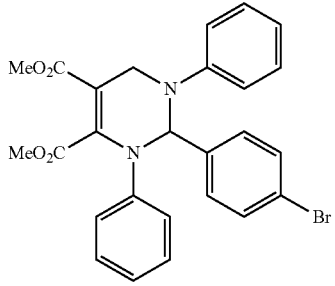 [SMILES: COC(=O)C1=C(C(=O)OC)N(c2ccccc2)C(c2ccc(Br)cc2)N(c2ccccc2)C1]

dimethyl-2-(4-bromophenyl)-1,2,3,6-tetrahydro-1,3-diphenylpyrimidine-4,5-dicarboxylate, Compound 31; yield=51%, yellow solid, melting point=164.5-165.9° C.; R (KBr): ν$_{max}$=2981, 2352, 1739, 1697, 1592, 1495, 1372, 1293, 1236, 1107, 1009, 910, 747, 696 cm⁻¹; ¹H NMR (400 MHz, CDCl₃): δ=7.59-6.90 (m, 14H), 6.04 (s, 1H), 4.27 (d, J=18.0 Hz, 1H), 3.66 (s, 3H), 3.64 (s, 3H), 3.57 (d, J=18.0 Hz, 1H) ppm; ¹³C NMR (101 MHz, CDCl₃): δ=165.71, 164.81, 149.23, 144.68, 144.15, 137.37, 132.32, 129.43, 129.34, 128.86, 126.23, 123.83, 122.59, 121.82, 119.03, 101.91, 79.43, 52.68, 51.58, 42.69 ppm; MS (ESI): m/z 507 (M+H⁺, 49), 509 (M+H⁺, 51), 248 (100); Anal. Calcd for C₂₆H₂₃BrN₂O₄: C, 61.55; H, 4.57; N, 5.52. Found: C, 61.38; H, 4.62; N, 5.47.

Example 32

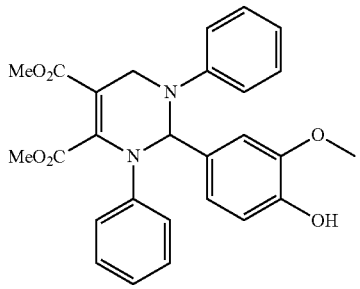 [SMILES: COC(=O)C1=C(C(=O)OC)N(c2ccccc2)C(c2ccc(O)c(OC)c2)N(c2ccccc2)C1]

dimethyl 1,2,3,6-tetrahydro-2-(4-hydroxy-3-methoxyphenyl)-1,3-diphenylpyrimidine-4,5-dicarboxylatea, Compound 32; yield=52%, yellow solid, melting point=158.5-160.1° C.; IR (KBr): ν$_{max}$=3061, 2950, 1740, 1697, 1580, 1514, 1495, 1434, 1282, 1237, 1115, 762, 696 CM⁻¹; ¹H NMR (400 MHz, CDCl₃): δ=7.25-6.89 (m, 13H), 6.09 (s, 1H), 5.72 (s.1H), 4.26 (d, J=18.0 Hz, 1H), 3.88 (s, 3H), 3.66 (s, 3H), 3.65 (s, 3H), 3.60 (d, J=18.0 Hz, 1H) ppm; ¹³C NMR (101 MHz, CDCl₃): δ=165.81, 165.03, 149.42, 146.98, 145.62, 144.62, 144.39, 130.06, 129.34, 129.24, 125.89, 123.51, 121.47, 119.86, 118.90, 114.88, 109.48, 102.12, 79.40, 56.04, 52.57, 51.47, 42.74 ppm; MS (ESI): m/z 475 (M+H⁺, 31), 248 (100); Anal. Calcd for C₂₇H₂₆N₂O₆: C, 68.34; H, 5.52; N, 5.90. Found: C, 68.48; H, 5.61; N, 5.88.

Example 33

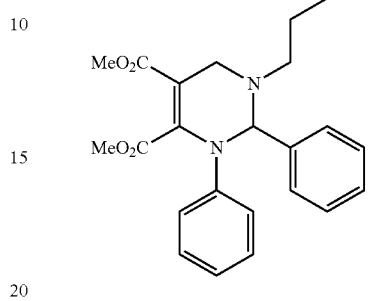

1-butyl-1,2,3,6-tetrahydro-2,3-diphenylpyrimidine-4,5-dicarboxylate, Compound 33; yield=21%, white solid, melting point=122.1-122.6° C.; IR (KBr): ν$_{max}$=2951, 1742, 1700, 1578, 1495, 1407, 1240, 1108, 750, 698 cm⁻¹; ¹H NMR (400 MHz, CDCl₃): δ=7.61~7.14 (m, 10H), 5.33 (s, 1H), 3.70 (s, 3H), 3.65 (s, 3H), 3.49 (d, J=18.4 Hz, 1H), 3.19 (d, J=17.8 Hz, 1H), 2.78-2.75 (m, 2H), 1.53-1.42 (m, 4H), 0.93 (t, J=7.2 Hz, 3H) ppm; ¹³C NMR (101 MHz, CDCl₃): δ=166.70, 165.06, 144.80, 144.15, 139.30, 129.25, 128.85, 128.07, 127.08, 125.88, 123.84, 99.18, 81.13, 52.90, 52.55, 51.28, 43.13, 30.20, 20.38, 13.97 ppm; MS (ESI): m/z 409 (M+H⁺, 50), 228 (100); Anal. Calcd for C₂₄H₂₈N₂O₄: C, 70.57; H, 6.91; N, 6.86. Found: C, 70.33; H, 6.79; N, 6.93.

Example 34

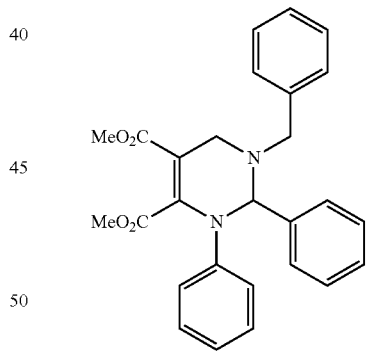

dimethyl 1-benzyl-1,2,3,6-tetrahydro-2,3-diphenylpyrimidine-4,5-dicarboxylate, Compound 34; yield=19%, white solid, melting point=133.0-134.1° C.; IR (KBr): ν$_{max}$=3030, 2949, 1742, 1699, 1578, 1495, 1434, 1359, 1290, 1244, 1110, 1058, 910, 735, 698 cm⁻¹; ¹H NMR (400 MHz, CDCl₃): δ=7.73-7.08 (m, 15H), 5.25 (s, 1H), 3.94 (s, 2H), 3.75 (s, 3H), 3.64 (s, 3H), 3.53 (d, J=18.0 Hz, 1H), 3.32 (d, J=17.6 Hz, 1H)ppm; ¹³C NMR (101 MHz, CDCl₃): δ=166.58, 165.11, 144.69, 143.93, 129.24, 128.93, 128.86, 128.37, 128.15, 127.37, 127.07, 125.75, 123.49, 99.82, 79.47, 57.57, 52.65, 51.33, 43.88 ppm; MS (ESI): m/z 443 (M+H+, 45), 262 (100); Anal. Calcd for C27H26N2O4: C, 73.28; H, 5.92; N, 6.33. Found: C, 73.11; H, 5.76; N, 6.28.

The AIE properties of Compound 1~34 were evaluated in the following examples, by the measurement of the ultraviolet absorption and fluorescence emission spectra as well as the fluorescence quantum yields of these compounds in solutions and in suspensions.

Example 35

Figure 5:
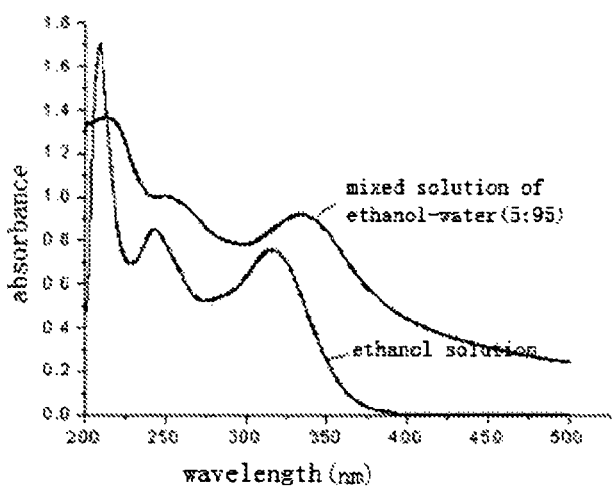
FIG. 5 shows the ultraviolet absorption spectrum of the compound emitting blue fluorescence at λ=365 nm in Example 1 in an ethanol solution and in a mixed solution of ethanol and water (5:95).
Figure 6:
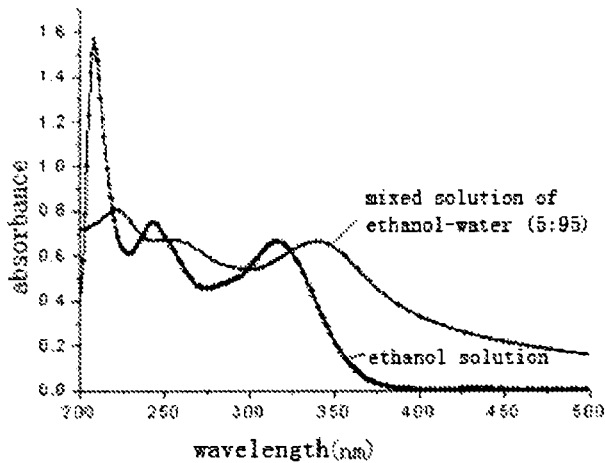
FIG. 6 shows the ultraviolet absorption spectrum of the compound emitting green fluorescence at λ=365 nm, in Example 1 in an ethanol solution and in a mixed solution of ethanol and water (5:95).

Measurement of ultraviolet absorption and fluorescence emission spectra of the compound in solutions:

The sample was prepared as an ethanol solution with concentration of $5 \times 10^{-5}$M. The ultraviolet absorption spectrum of the solution was determined using ultraviolet and visible spectrophotometer TU-901 of Yitong company, Beijing. The ultraviolet absorption spectra of the Compound 1 emitting blue fluorescence at λ=365 nm in Example 1 in an ethanol solution and a mixed solution of ethanol and water (5:95) were shown in FIG. 5. The ultraviolet absorption spectra of the Compound 1 emitting green fluorescence at λ=365 nm in Example 1 in an ethanol solution and a mixed solution of ethanol and water (5:95) were shown in FIG. 6.

Figure 7:
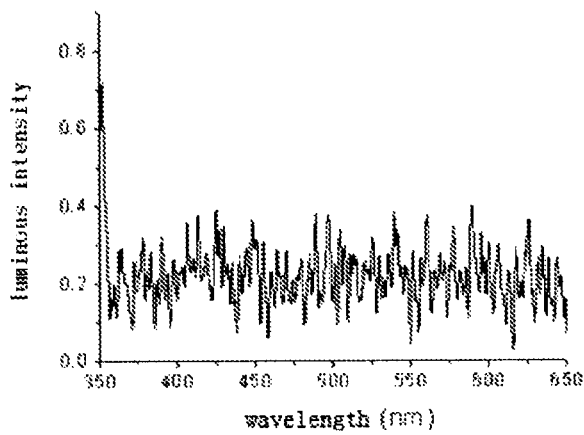
FIG. 7 shows the fluorescence emission spectra of the compound emitting blue fluorescence at λ=365 nm in Example 1 in an ethanol solution.
Figure 8:
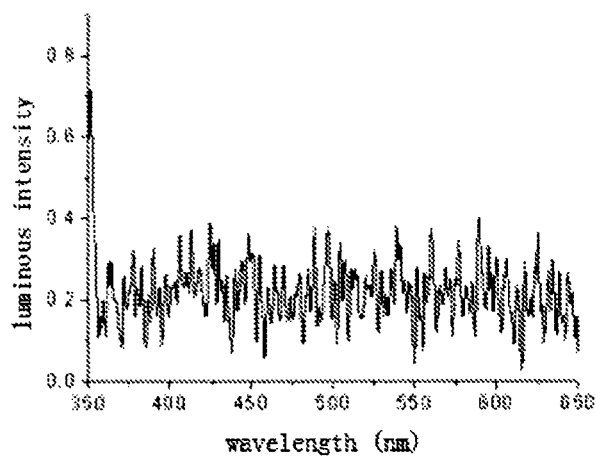
FIG. 8 shows the fluorescence emission spectra of the compound emitting green fluorescence at λ=365 nm in Example 1 in an ethanol solution.

The fluorescence emission spectrum of the solution was determined using fluorescence spectrophotometer RF5301PC of Shimadzu company, Japan. The fluorescence emission spectrum of the Compound 1 emitting blue fluorescence at λ=365 nm in Example 1 in an ethanol solution was shown in FIG. 7. The fluorescence emission spectrum of the Compound 1 emitting green fluorescence at λ=in Example 1 in an ethanol solution was shown in FIG. 8.

Figure 9:
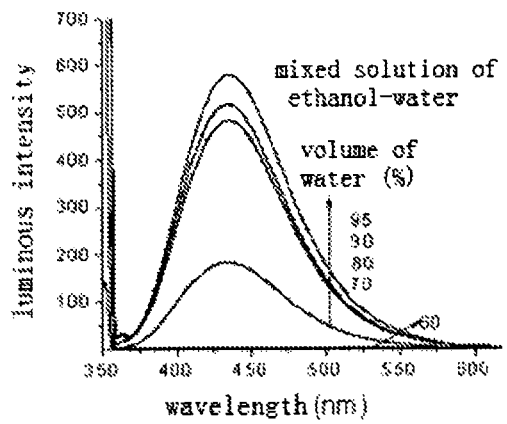
FIG. 9 shows the fluorescence emission spectra of the compound emitting blue fluorescence at λ=365 nm in Example 1 in a mixed solution of ethanol and water of different ratios.
Figure 10:
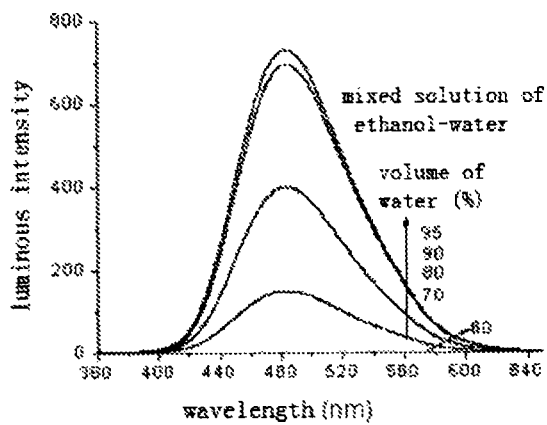
FIG. 10 shows the fluorescence emission spectra of the compound emitting green fluorescence at λ=365 nm in Example 1 in a mixed solution of ethanol and water of different ratios.

Measurement of fluorescence emission spectrum of the compound in suspensions:

Water, a poor solvent, was added slowly into ethanol solution of the sample under ultrasonic vibration to prepare a suspension of ethanol-water (40:60-5:95) with a final concentration of $5 \times 10^5$M. The fluorescence emission spectra of the suspension were determined using fluorescence spectrophotometer RF5301PC of Shimadzu company, Japan. The fluorescence emission spectra of the Compound 1 emitting blue fluorescence at λ=365 nm in Example 1 in nanoparticle suspensions of ethanol-water with different ratios were shown in FIG. 9. The fluorescence emission spectra of the Compound 1 emitting green fluorescence at λ=365 nm in Example 1 in nanoparticle suspensions with different ratios were shown in FIG. 10.

Measurement of fluorescence quantum yields (Φ) of the compound in solutions and in suspensions:

Dilute solution method was used to determine the fluorescence quantum yield with reference of 9,10-diphenylanthracene (DPA) (ethanol solution, $\Phi_{DPA}$=0.95). The quantum yield was calculated by the following equation:

$$\Phi_{unknown} = \frac{S_{unknown} A_{DPA}}{S_{DPA} A_{unknown}} \Phi_{DPA}$$

In the equation, $\Phi_{unknown}$ indicates the fluorescence quantum yield of the unknown sample; $\Phi_{DPA}$ indicates the fluorescence quantum yield of the reference DPA ($\Phi_{DPA}$=0.95) $S_{unknown}$ and $S_{DPA}$ is respectively the integral area of the fluorescence emission spectrum of the sample and the reference at 350 nm wavelength; $A_{unknown}$ and $A_{DPA}$ is respectively the absorbance of the sample and the reference at 350 nm wavelength.

Figure 11:
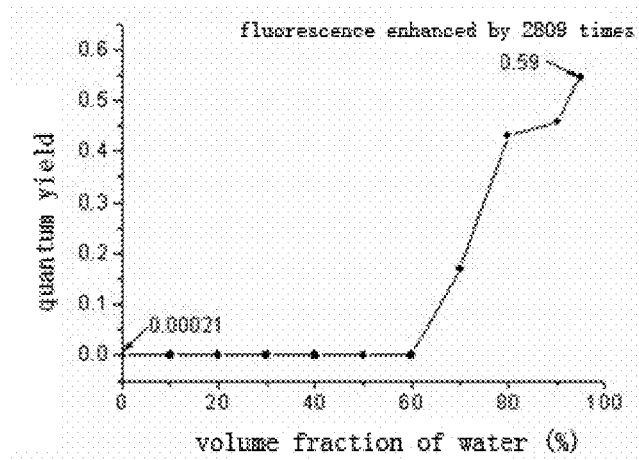
FIG. 11 shows the fluorescence quantum yield of the compound emitting blue fluorescence at λ=365 nm in Example 1 in a mixed solution of ethanol and water of different ratios.

The fluorescence quantum yield of the Compound 1 emitting blue fluorescence at λ=365 nm in mixed solutions of ethanol-water with different ratios were shown in FIG. 11.

Figure 12:
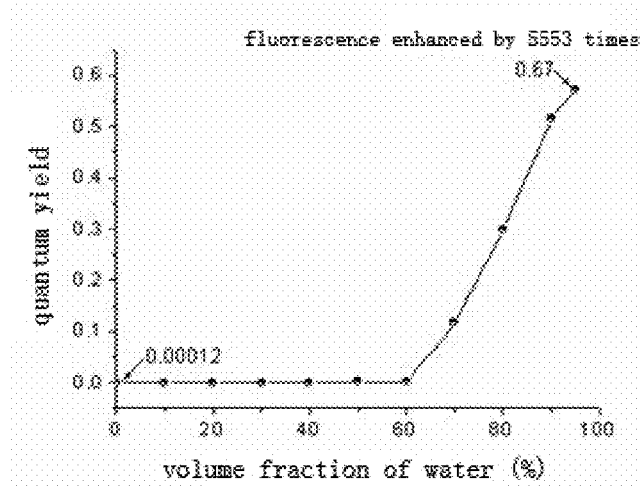
FIG. 12 shows the fluorescence quantum yield of the compound emitting green fluorescence at λ=365 nm in Example 1 in a mixed solution of ethanol and water of different ratios.

The fluorescence quantum yield of the Compound 1 emitting green fluorescence at λ=365 nm in mixed solutions of ethanol-water with different ratios were shown in FIG. 12.

The maximum absorption wavelength ($A_{max}^{ab}$), molar absorption coefficient (ε) and quantum yield ($\Phi_s$) of the Compounds 1~32 in Examples 1~32 with a concentration of $5 \times 10^{-5}$M in ethanol solutions, the maximum emission wavelength ($\lambda_{max}^{em}$) and quantum yield ($\Phi_a$) of the Compounds 1~32 in mixed solutions of ethanol-water (1:9), and the ratio of the quantum yields of the Compounds 1~32 in mixed solutions of ethanol-water (1:9) and in ethanol solutions are shown in Table 1.

TABLE 1 optical performance of Compounds 1~34

| Compound No. | $\lambda_{max}^{ab}$/ nm [a] | ε/ cm$^{-1}$· M$^{-1}$ | $\lambda_{max}^{em}$/ nm [b] | $\Phi_s$ [c] | $\Phi_a$ [c] | $\Phi_d/\Phi_s$ |
|---|---|---|---|---|---|---|
| 1- blue crystal | 317 | 34408 | 436 | 0.00021 | 0.59 | 2809 |
| 1- green crystal | 318 | 31410 | 483 | 0.00012 | 0.67 | 5553 |
| 2 | 297 | 15044 | 452 | 0.00629 | 0.1052 | 16.7 |
| 3 | 318 | 30506 | 482 | 0.00132 | 0.05773 | 43.7 |
| 4 | 320 | 35606 | 470 | 0.001966 | 0.5531 | 281.3 |
| 5 | 320 | 39112 | 478 | 0.000604 | 0.2602 | 430.8 |
| 6 | 317 | 33192 | 477 | 0.000484 | 0.4626 | 955.8 |
| 7 | 317 | 45598 | 484 | 0.000398 | 0.1208 | 303.5 |
| 8 | 316 | 38448 | 475 | 0.000324 | 0.7122 | 2198 |
| 9 | 319 | 40876 | 465 | 0.000382 | 0.02423 | 63.4 |
| 10 | 318 | 20866 | 473 | 0.00048 | 0.04764 | 99 |
| 11 | 315 | 13742 | 455 | 0.00355 | 0.366 | 103 |
| 12 | 318 | 25840 | 472 | 0.00016 | 0.04930 | 308 |
| 13 | 321 | 26104 | 441 | 0.000477 | 0.7792 | 1633 |
| 14 | 320 | 41610 | 466 | 0.000356 | 0.01877 | 52.7 |
| 15 | 321 | 33252 | 488 | 0.000726 | 0.2106 | 290 |
| 16 | 317 | 11752 | 488 | 0.003391 | 0.6072 | 179 |
| 17 | 320 | 33792 | 475 | 0.000510 | 0.6544 | 1283 |
| 18 | 316 | 35828 | 482 | 0.0005 | 0.4952 | 990 |
| 19 | 315 | 25736 | 476 | 0.000134 | 0.5948 | 4438 |
| 20 | 314 | 24966 | 452 | 0.001283 | 0.03346 | 26 |
| 21 | 318 | 25998 | 486 | 0.00107 | 0.1299 | 121 |
| 22 | 316 | 24778 | 485 | 0.000118 | 0.2437 | 2065 |
| 23 | 317 | 39926 | 492 | 0.000449 | 0.4603 | 1025 |
| 24 | 319 | 30982 | 475 | 0.000384 | 0.8059 | 2099 |
| 25 | 320 | 32984 | 477 | 0.000308 | 0.3822 | 1240 |
| 26 | 317 | 29556 | 454 | 0.000936 | 0.3584 | 382 |
| 27 | 317 | 33914 | 483 | 0.000881 | 0.2295 | 260 |
| 28 | 301 | 100500 | 469 | 0.00293 | 0.0364 | 12.5 |
| 29 | 312 | 27250 | 475 | 0.000318 | 0.1384 | 435 |
| 30 | 310 | 13388 | 460 | 0.00193 | 0.3933 | 204 |
| 31 | 316 | 29674 | 487 | 0.000913 | 0.4437 | 485 |
| 32 | 318 | 38994 | 471 | 0.000397 | 0.04525 | 114 |
| 33 | 316 | 15044 | 411 | 0.00926 | 0.3723 | 40.2 |
| 34 | 335 | 5754 | 450 | 0.003 | 0.0644 | 21.5 |

[a] ethanol solution of the sample;
[b] mixed solution of ethanol-water (1:9) of the sample;
[c] using 9,10-diphenylanthracene (concentration = $5 \times 10^{-5}$ M, quantum yield in ethanol solution Φ = 0.95, excitation wavelength = 350 nm) as standard substance to calculate the quantum yield;
[d] mixed solution of ethanol-water (5:95) of the sample.

It can be seen from Table 1 that Compounds 1~34 have AIE properties ($\Phi_a/\Phi_s$ is larger than 12.5, and most of the ratios are larger than 100) and good light-absorbing property (ε=5754~100500 cm$^{-1}$·M$^{-1}$) and quantum yields up to 0.81. The ratios between the fluorescence quantum yields of Compounds 1, 8, 13, 17, 19, 22-25 in aggregates and those in solutions are larger than 1000, indicating very strong AIE properties. Therefore, this series of compounds are a series of AIE substances with good optical properties.

What is claimed is:

1. A penta-substituted tetrahydropyrimidines with aggregation-induced emission characteristics, comprising structures shown as formula (I):

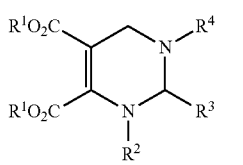 (I)

wherein $R^1$ is selected from a group consisting of linear or branched $C_{1-8}$ alkyls and substituted $C_{1-8}$ alkyls;

$R^2$ and $R^4$ are independently selected from a group consisting of $C_{1-8}$ linear or branched alkyls, $C_{1-8}$ substituted alkyls, $C_{5-8}$ cycloalkyls, $C_{5-8}$ substituted cycloalkyls, $C_{5-6}$ aryls, $C_{5-6}$ substituted aryls, $C_{9-18}$ polycyclic aryls, $C_{9-18}$ substituted polycyclic aryls, $C_{5-6}$ heterocyclyls, $C_{5-6}$ substituted heterocyclyls, $C_{5-6}$ aromatic heterocyclyls and $C_{5-6}$ substituted aromatic heterocyclyls;

$R^3$ is selected from a group consisting of $C_{5-6}$ aryls, $C_{5-6}$ substituted aryls, $C_{9-18}$ polycyclic aryls, $C_{9-18}$ substituted polycyclic aryls, $C_{5-6}$ aromatic heterocyclyls and $C_{5-6}$ substituted aromatic heterocyclyls.

2. The penta-substituted tetrahydropyrimidines with aggregation-induced emission characteristics of claim 1, wherein $R^1$ is selected from a group consisting of $C_{1-2}$ alkyls.

3. The penta-substituted tetrahydropyrimidines with aggregation-induced emission characteristics of claim 1, wherein $R^2$ is selected from a group consisting of $C_{1-5}$ linear or branched alkyls, $C_{1-5}$ substituted alkyls, $C_{5-8}$ cycloalkyls, $C_{5-6}$ aryls and $C_{5-6}$ substituted aryls.

4. The penta-substituted tetrahydropyrimidines with aggregation-induced emission characteristics of claim 1, wherein $R^3$ is selected from a group consisting of $C_{5-6}$ aryls and $C_{5-6}$ substituted aryls.

5. The penta-substituted tetrahydropyrimidines with aggregation-induced emission characteristics of claim 1, wherein $R^4$ is selected from a group consisting of $C_{1-5}$ linear or branched alkyls, $C_{1-5}$ substituted alkyls, $C_{5-8}$ cycloalkyls, $C_{5-6}$ aryls and $C_{5-6}$ substituted aryls.

6. The penta-substituted tetrahydropyrimidines with aggregation-induced emission characteristics of claim 1, wherein the substituents are selected from a group consisting of halogens, $C_{1-2}$ perhalogenated alkyls, $C_{1-4}$ halogenated alkyls, hydroxyl, $C_{1-6}$ linear or branched alkoxys, nitryl, cyano, amino, $C_{1-6}$ monoalkyl aminos, $C_{1-6}$ dialkyl aminos, $C_{5-8}$ monocyclic alkyl aminos, $C_{5-6}$ monoheterocyclyl aminos, $C_{5-6}$ monoaryl aminos, $C_{1-6}$ alkyl aminos, $C_{5-6}$ aryl amidos, amino carbonyls, $C_{1-6}$ monoalkyl amino carbonyls, $C_{1-6}$ dialkyl amino carbonyls, $C_{1-6}$ alkyl acyls, $C_{5-8}$ aryl acyls, amino sulfones, $C_{1-6}$ monoalkyl amino sulfones, $C_{1-6}$ dialkyl amino sulfones, $C_{5-8}$ aryl amino sulfones, $C_{1-6}$ alkyl sulfonyl aminos, carboxyl, $C_{1-6}$ monoalkyl sulfones, linear or branched alkyls, $C_{5-8}$ cycloalkyls, $C_{5-8}$ substituted cycloalkyls, $C_{2-4}$ alkenyls, $C_{2-4}$ alkynyls, aryl $C_{1-3}$ alkyls, $C_{5-6}$ aryls, $C_{5-6}$ substituted aryls, $C_{9-18}$ polycyclic aryls, $C_{5-6}$ heterocyclyls, $C_{5-6}$ aromatic heterocyclyls and $C_{9-18}$ polycyclic aromatic heterocyclyls.

7. The penta-substituted tetrahydropyrimidines with aggregation-induced emission characteristics of claim 1, wherein in formula (I), $R^1$ is methyl or ethyl;

$R^2$ is selected from a group consisting of phenyl, benzyl, methyl phenyl, chlorophenyl, bromophenyl, trifluoromethyl phenyl, n-butyl;

$R^3$ is selected from a group consisting of phenyl, bromophenyl, methoxy hydroxy substituting phenyl, bromophenyl, trifluoromethyl phenyl, naphthyl, pyridyl; and $R^4$ is selected from a group consisting of phenyl, benzyl, methyl phenyl, chlorophenyl, bromophenyl, trifluoromethyl phenyl, hydroxyethyl, n-butyl.

8. A method of preparing the penta-substituted tetrahydropyrimidines with aggregation-induced emission characteristics of any claim 1, comprising steps of (by mmol parts):

(1) adding 1 part of formula (II) compound and 1 part of formula (III) compound into 1~10 mL of organic solvent, followed by stirring at 0~60° C. for 10~60 minutes;

(2) adding 1~5 parts of formula (IV) compound, 1~5 parts of formaldehyde and then 0~4 parts of acid into 1~10 mL of organic solvent, followed by stirring at 20~100° C. for 10 minutes ~5 hours;

(3) mixing solutions obtained by steps (1) and (2), then adding 1~5 parts of formula (V) compound and 0.1~0.5 parts of catalyst, followed by stirring at −15~100° C. for 1~7 days, separating and purifying to obtain a product;

wherein

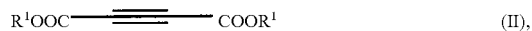 (II), $R^2NH_2$ (III), $R^4NH_2$ (IV), $R^3CHO$ (V);

the acid being hydrochloric acid, sulfuric acid, phosphoric acid, benzenesulfonic acid, trifluoroacetic acid, acetic acid or a mixture thereof;

the catalyst being copper sulfate, copper acetate, zinc chloride, palladium acetate, thiourea, praline, urea or a mixture thereof;

the organic solvent being ethanol, benzene, toluene, hexane, halogenated hydrocarbons, ethers, N,N-dimethylformamide, dimethyl sulfoxide, acetonitrile or a mixture thereof.

9. A method of using the penta-substituted tetrahydropyrimidines with aggregation-induced emission characteristics of any claim 1 in preparing organic electro-luminescence or photo-luminescence devices.

10. A method of using the penta-substituted tetrahydropyrimidines with aggregation-induced emission characteristics of claim 1 in preparing chemical and biological fluorescent sensors or probes.

* * * * *